US011434533B2

(12) United States Patent
Saeki

(10) Patent No.: US 11,434,533 B2
(45) Date of Patent: Sep. 6, 2022

(54) METHOD FOR DETECTING TARGET NUCLEIC ACID AND NUCLEIC ACID PROBE USED THEREIN

(71) Applicant: EIKEN KAGAKU KABUSHIKI KAISHA, Tokyo (JP)

(72) Inventor: Ryohei Saeki, Otawara (JP)

(73) Assignee: EIKEN KAGAKU KABUSHIKI KAISHA, Tokyo (JP)

( * ) Notice: Subject to any disclaimer, the term of this patent is extended or adjusted under 35 U.S.C. 154(b) by 442 days.

(21) Appl. No.: 16/075,709

(22) PCT Filed: Feb. 6, 2017

(86) PCT No.: PCT/JP2017/004191
§ 371 (c)(1),
(2) Date: Aug. 6, 2018

(87) PCT Pub. No.: WO2017/138484
PCT Pub. Date: Aug. 17, 2017

(65) Prior Publication Data
US 2019/0055600 A1 Feb. 21, 2019

(30) Foreign Application Priority Data
Feb. 9, 2016 (JP) .............................. JP2016-022659

(51) Int. Cl.
C07H 21/04 (2006.01)
C12Q 1/68 (2018.01)
C12Q 1/6876 (2018.01)
G01N 21/78 (2006.01)
C12N 15/09 (2006.01)
C12Q 1/6844 (2018.01)
G01N 21/64 (2006.01)

(52) U.S. Cl.
CPC ........... *C12Q 1/6876* (2013.01); *C12N 15/09* (2013.01); *C12Q 1/68* (2013.01); *C12Q 1/6846* (2013.01); *G01N 21/6428* (2013.01); *G01N 21/78* (2013.01); *G01N 2021/6432* (2013.01); *G01N 2021/6439* (2013.01)

(58) Field of Classification Search
None
See application file for complete search history.

(56) References Cited

U.S. PATENT DOCUMENTS

| 5,210,015 | A | 5/1993 | Gelfand et al. |
| 6,699,661 | B1 | 3/2004 | Kurane et al. |
| 7,803,528 | B1 | 9/2010 | Chiang et al. |
| 10,793,855 | B2 * | 10/2020 | Rigo .................... A61K 9/0085 |
| 2002/0106653 | A1 | 8/2002 | Kurane et al. |
| 2004/0023269 | A1 | 2/2004 | Li et al. |
| 2004/0054160 | A1 * | 3/2004 | Pal ....................... C12Q 1/6806 536/24.3 |
| 2004/0197802 | A1 * | 10/2004 | Dahl ..................... C12Q 1/6853 435/6.11 |
| 2005/0282179 | A1 * | 12/2005 | Martin ............... G01N 33/5767 435/7.1 |
| 2009/0176231 | A1 | 7/2009 | Hirai et al. |
| 2010/0047806 | A1 * | 2/2010 | Hirai ..................... C12Q 1/6827 435/6.16 |
| 2012/0009576 | A1 | 1/2012 | Hosomi |
| 2012/0058481 | A1 * | 3/2012 | Ge ......................... C12Q 1/686 435/6.12 |
| 2012/0107817 | A1 * | 5/2012 | Iguchi .................. C12Q 1/6886 435/6.11 |
| 2012/0231463 | A1 | 9/2012 | Hirai et al. |
| 2013/0078631 | A1 | 3/2013 | Komori |
| 2013/0084568 | A1 | 4/2013 | Kurose et al. |
| 2014/0251809 | A1 * | 9/2014 | Sakamoto ........ G01N 27/44756 204/465 |

(Continued)

FOREIGN PATENT DOCUMENTS

| CN | 1938328 A | 3/2007 |
| CN | 101137759 A | 3/2008 |
| CN | 102242211 A | 11/2011 |

(Continued)

OTHER PUBLICATIONS

Notification of Transmittal of Translation of the International Preliminary Report on Patentability (Form PCT/IB/338) issued in counterpart International Application No. PCT/JP2017/004191 dated Aug. 23, 2018, with Forms PCT/IB/373 and PCT/ISA/237. (9 pages).

Tani, Hidenori et al., "Technique for Quantitative Detection of Specific DNA Sequences Using Alternately Binding Quenching Probe Competitive Assay Combined with Loop-Mediated Isothermal Amplification", Analytical Chemistry, Aug. 1, 2007, vol. 79, No. 15, pp. 5608-5613, Cited in Extended EP Search Report dated Jun. 18, 2019.

Extended Search Report dated Jun. 18, 2019, issued in counterpart EP Application No. 17750207.7 (10 pages).

Office Action dated May 7, 2019, issued in counterpart JP Application No. 2017-566932, with English translation. (11 pages).

(Continued)

Primary Examiner — Bradley L. Sisson
(74) Attorney, Agent, or Firm — WHDA, LLP

(57) ABSTRACT

Disclosed herein is a nucleic acid probe for detecting a target nucleic acid. At least one terminal of the probe-binding region in the target nucleic acid is a guanine base, and one or more cytosine bases are present within 1 to 7 bases from the guanine base. The nucleic acid probe comprises an oligonucleotide having a cytosine base facing the guanine base on a terminal and a fluorescent dye conjugated to the cytosine base. The fluorescent dye is quenched by the interaction with a guanine base. The oligonucleotide is completely complementary to the nucleic acid in the probe-binding region except the one or more cytosine bases present within 1 to 7 bases from the terminal guanine base. The base in the oligonucleotide facing the cytosine base closest to the terminal guanine base among the one or more cytosine bases is a base having no fluorescence-quenching effect.

8 Claims, 9 Drawing Sheets
Specification includes a Sequence Listing.

(56) References Cited

U.S. PATENT DOCUMENTS

2016/0053309 A1 2/2016 Kitani et al.

FOREIGN PATENT DOCUMENTS

| CN | 102449167 A | 5/2012 |
|---|---|---|
| CN | 103122374 A | 5/2013 |
| EP | 1307592 A2 | 5/2003 |
| EP | 1 307 592 B1 | 7/2006 |
| JP | 6-500021 A | 1/1994 |
| JP | 10-262700 A | 10/1998 |
| JP | 2001-286300 A | 10/2001 |
| JP | 2002-000275 A | 1/2002 |
| JP | 2004-506431 A | 3/2004 |
| JP | 2004-511227 A | 4/2004 |
| JP | 2008-199965 A | 9/2008 |
| JP | 2010-273660 A | 12/2010 |
| JP | 2012-34688 A | 2/2012 |
| JP | 2013-81450 A | 5/2013 |
| JP | 2013-90622 A | 5/2013 |
| JP | 2015-128400 A | 7/2015 |
| WO | 02/14555 A2 | 2/2002 |
| WO | 2006/082685 A1 | 8/2006 |
| WO | 2006/088126 A1 | 8/2006 |
| WO | 2014/157377 A1 | 10/2014 |

OTHER PUBLICATIONS

International Search Report dated Apr. 25, 2017, issued in counterpart International Application No. PCT/JP2017/004191. (2 pages).
Kurata, Shinya et al., "Fluorescent quenching-based quantitative detection of specific DNA/RNA using a BODIPY FL-labeled probe or primer", Nucleic Acids Research 2001 Oxford University Press, 2001, vol. 29, No. 6, pp. 34.1-5; Cited in JP Office Action dated Dec. 8, 2020. (5 pages).
Suzuki, Shun-ichi et al., "Development of a Novel, Fully-Automated Genotyping System: Principle and Applications", Sensors, vol. 12, No. 12, Dec. 3, 2012; CN Office Action dated Apr. 16, 2021. (14 pages).
Naohiro Noda,"Development of an accurate and cost-effective quantitative detection method for specific gene sequences", Synthesiology, 2010, vol. 3, No. 2, pp. 147-157, cited in Notification of Information issued from the JPO dated Aug. 3, 2021. (11 pages).
Notification of Information issued from the JPO dated Aug. 3, 2021, issued in counterpart JP application No. 2019-119734, with English translation. (19 pages).
Office Action dated Aug. 17, 2021, issued in counterpart JP application No. 2019-119734, with English translation. (9 pages).

\* cited by examiner

Fig. 1 (a) WHEN TARGET NUCLEIC ACID HAS PROBE-BINDING REGION
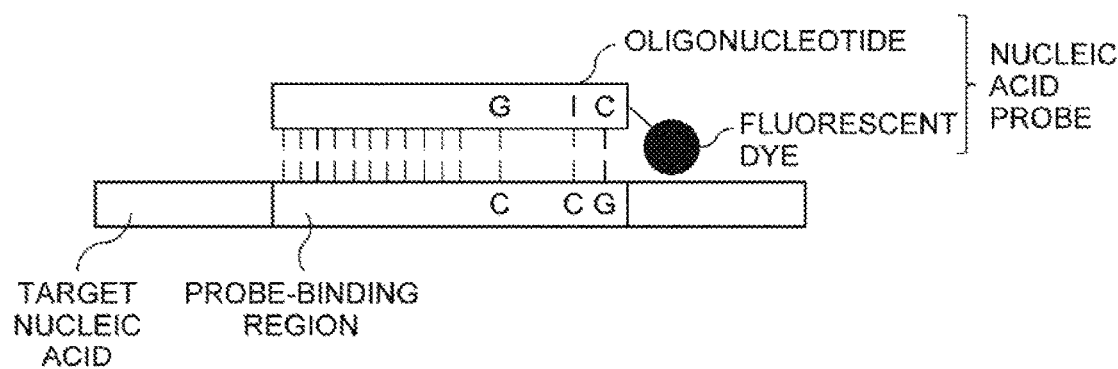
Fig. 1 (b) WHEN TARGET NUCLEIC ACID HAS NO PROBE-BINDING REGION
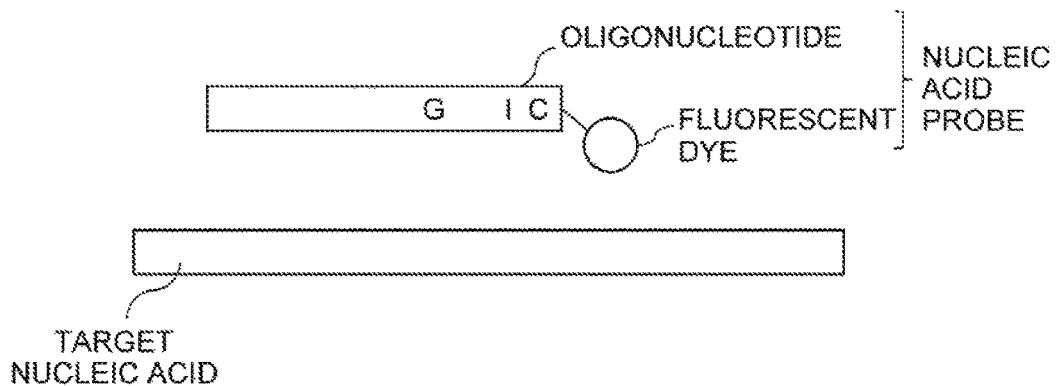

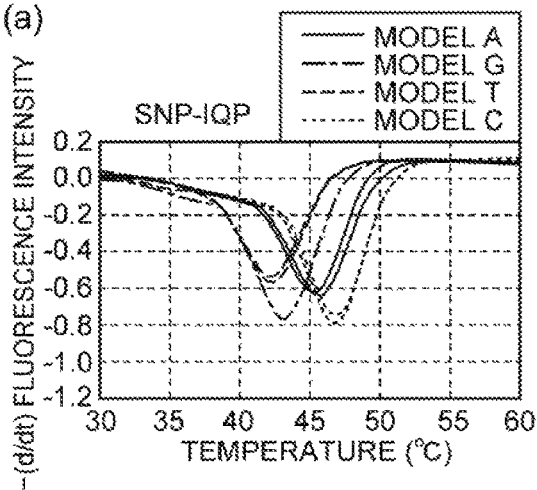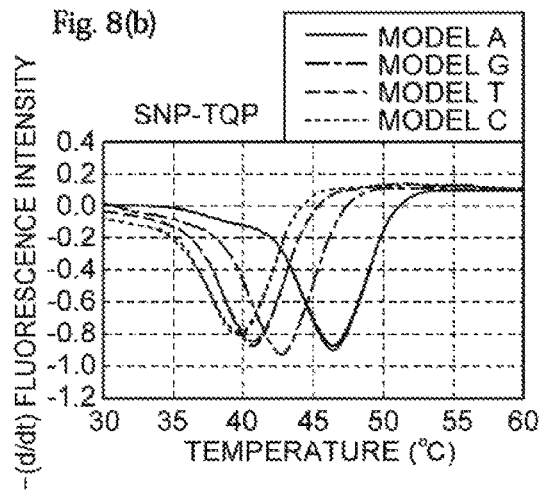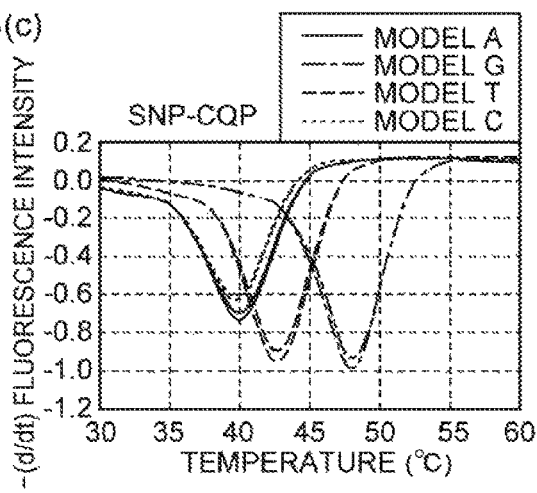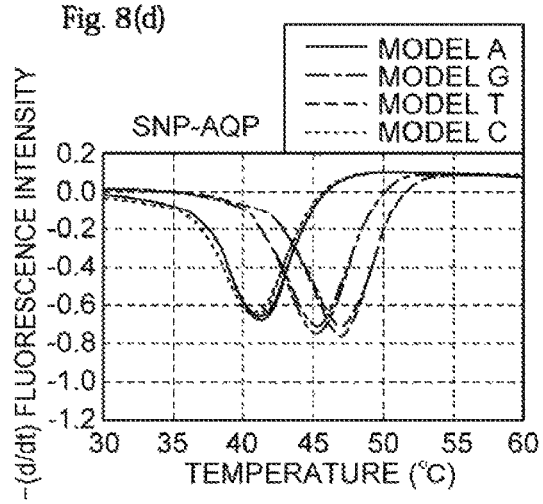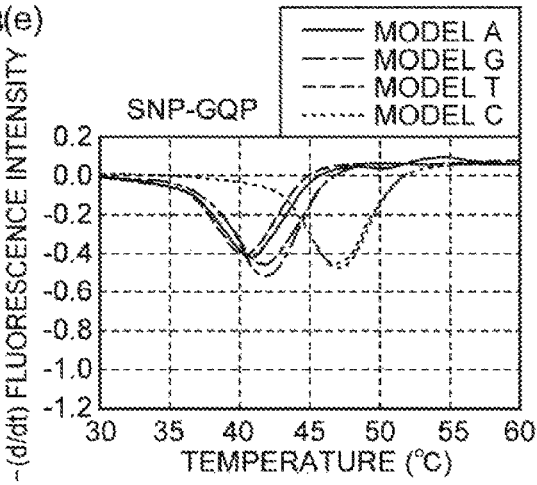

SEQUENCE LISTING

```
<160> NUMBER OF SEQ ID NOS: 50

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 1 gcttttttttt tttttttttt c                                              21

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 2
aaaaaaaaaa aaaaaaaagc                                                 20

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: modified_base
<222> LOCATION: (20)..(20)
<223> OTHER INFORMATION: I

<400> SEQUENCE: 3
gaaaaaaaaa aaaaaaaan c                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 4
gaaaaaaaaa aaaaaaaat c                                              21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
gaaaaaaaaa aaaaaaaac c                                              21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
gaaaaaaaaa aaaaaaaaa c                                              21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: Nebularine

<400> SEQUENCE: 7
gaaaaaaaaa aaaaaaaan c                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: 2-dimethylaminomethyleneamino-6-
      methoxyaminopurine

<400> SEQUENCE: 8
gaaaaaaaaa aaaaaaaan c                                              21

<210> SEQ ID NO 9
```

-continued

<210> SEQ ID NO 9
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: 3-Nitropyrrole

<400> SEQUENCE: 9
gaaaaaaaaa aaaaaaaaan c                                    21

<210> SEQ ID NO 10
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 10
gttctttttt tttttttttt c                                    21

<210> SEQ ID NO 11
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 11
gttttctttt tttttttttt c                                    21

<210> SEQ ID NO 12
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 12 gtttttttctt tttttttttt c                                   21

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13
aaaaaaaaaa aaaaaagaac                                      20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14
aaaaaaaaaa aaaagaaaac                                      20

<210> SEQ ID NO 15
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 15
aaaaaaaaaa aagaaaaaac                                              20

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (18)..(18)
<223> OTHER INFORMATION: I

<400> SEQUENCE: 16
gaaaaaaaaa aaaaaaanaa c                                            21

<210> SEQ ID NO 17
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(16)
<223> OTHER INFORMATION: I

<400> SEQUENCE: 17
gaaaaaaaaa aaaaanaaaa c                                            21

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (14)..(14)
<223> OTHER INFORMATION: I

<400> SEQUENCE: 18
gaaaaaaaaa aaanaaaaaa c                                            21

<210> SEQ ID NO 19
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 19 gcctttttttt tttttttttt cc                                          22

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
aaaaaaaaaa aaaaaaaggc                                              20
```

```
<210> SEQ ID NO 21
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: I

<400> SEQUENCE: 21
gaaaaaaaaa aaaaaaaagn c                                              21

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(21)
<223> OTHER INFORMATION: I

<400> SEQUENCE: 22
ggaaaaaaaa aaaaaaaaan nc                                             22

<210> SEQ ID NO 23
<211> LENGTH: 425
<212> TYPE: DNA
<213> ORGANISM: Mycoplasma pneumoniae

<400> SEQUENCE: 23
aattcgaatt tgaaggccca aggcctcacc caacccgcct acctcatcgc cggtcttgac     60
gttgtggccg accacctcgt ctttgcggcc tttaaagcgg gcgcggtggg gtatgatatg    120
acgactgatt cgagcgcttc gacctacaac caagcactcg cctggtcgac cacgccgggg    180
ttggacagtg atggggggta caaggccttg gtggaaaaca cggccgggct caacggcccg    240
attaatggct tgtttaccct gctcgacacc tttgcgtatg tgaccccgt gagtgggatg    300 aaaggggga gtcagaataa tgaagaagtg caaacgactt acccggtcaa gtccgaccaa    360
aaggccaccg ccaaaattgc ctccttaatt aatgccagcc cactcaacag ttatggggat    420
gatgg                                                                425

<210> SEQ ID NO 24
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 24
tccgaccaaa aggccaccgc c                                              21

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: I
```

<400> SEQUENCE: 25
gtccgaccaa aaggccaccn cc                                            22

<210> SEQ ID NO 26
<211> LENGTH: 664
<212> TYPE: DNA
<213> ORGANISM: Mycobacterium tuberculosis

<400> SEQUENCE: 26
agttggcgcg cgacctgcat ccggacgcga acccgggcaa cccggccgcc ggcgaacggt    60
tcaaggcggt ttcggaggcg cataacgtgc tgtcggatcc ggccaagcgc aaggagtacg   120
acgaaacccg ccgcctgttc gccggcggcg ggttcggcgg ccgtcggttc gacagcggct   180
ttgggggcgg gttcggcggt ttcggggtcg gtggagacgg cgccgagttc aacctcaacg   240
acttgttcga cgccgccagc cgaaccggcg gtaccaccat cggtgacttg ttcggtggct   300
tgttcggacg cggtggcagc gcccgtccca gccgcccgcg acgcggcaac gacctggaga   360
ccgagaccga gttggatttc gtggaggccg ccaagggcgt ggcgatgccg ctgcgattaa   420
ccagcccggc gccgtgcacc aactgccatg gcagcggggc ccggccaggc accagcccaa   480
aggtgtgtcc cacttgcaac gggtcgggcg tgatcaaccg caatcagggc gcgttcggct   540
tctccgagcc gtgcaccgac tgccgaggta gcggctcgat catcgagcac ccctgcgagg   600
agtgcaaagg caccggcgtg accacccgca cccgaaccat caacgtgcgg atcccgcccg   660
gtgt                                                               664

<210> SEQ ID NO 27
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 27
ccaagcgcaa ggagtacgac gaa                                           23

<210> SEQ ID NO 28
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 28
gaacaagcca ccgaacaagt caccgat                                       27

<210> SEQ ID NO 29
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 29
cggtggagac ggcgc                                                    15

<210> SEQ ID NO 30
<211> LENGTH: 17
<212> TYPE: DNA
<213> ORGANISM: Artificial Sequence
<220> FEATURE:

```
<223> OTHER INFORMATION: Synthetic oligonucleotide
<220> FEATURE:
<221> NAME/KEY: modified_base
<222> LOCATION: (16)..(16)
<223> OTHER INFORMATION: I

<400> SEQUENCE: 30
gtcggtggag acggcnc                                                17

<210> SEQ ID NO 31
<211> LENGTH: 18
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (15)..(15)
<223> OTHER INFORMATION: I
<220> FEATURE:
<221> NAME/KEY: modified_base
<222> LOCATION: (17)..(17)
<223> OTHER INFORMATION: I

<400> SEQUENCE: 31
ggtcggtgga gacgncnc                                               18

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 32
gatttttttt tttttttttt c                                           21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 33
ggtttttttt tttttttttt c                                           21

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 34 gtttttttttt tttttttttt c                                          21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 35 gcttttttttt tttttttttt c                                          21
```

```
<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 36
gaaaaaaaaa aaaaaaaaag c                                               21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (20)..(20)
<223> OTHER INFORMATION: I

<400> SEQUENCE: 37
gaaaaaaaaa aaaaaaaaan c                                               21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 38
gaaaaaaaaa aaaaaaaaaa c                                               21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 39
gaaaaaaaaa aaaaaaaaat c                                               21

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 40
gaaaaaaaaa aaaaaaaaac c                                               21

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 41 gttattttttt tttttttttt c                                              21

<210> SEQ ID NO 42
<211> LENGTH: 21
<212> TYPE: DNA
```

```
<213> ORGANISM: Artificial Sequence
<220> FEATURE:
<223> OTHER INFORMATION: Synthetic oligonucleotide

<400> SEQUENCE: 42
gttgtttttt ttttttttt c                                              21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 43
gttttttttt ttttttttt c                                              21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 44 gttcttttttt ttttttttt c                                             21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (18)..(18)
<223> OTHER INFORMATION: I

<400> SEQUENCE: 45
gaaaaaaaaa aaaaaaanaa c                                             21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 46
gttttatttt ttttttttt c                                              21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 47
gttttgtttt ttttttttt c                                              21

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide
```

```
<400> SEQUENCE: 48
gttttttttt ttttttttttt c                                               21

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49 gttttcttt ttttttttttt c                                                21

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: modified_base
<222> LOCATION: (16)..(16)
<223> OTHER INFORMATION: I

<400> SEQUENCE: 50
gaaaaaaaaa aaaaanaaaa c                                                21
```

METHOD FOR DETECTING TARGET NUCLEIC ACID AND NUCLEIC ACID PROBE USED THEREIN

CROSS-REFERENCE TO RELATED APPLICATIONS

This application is a 371 National Stage of International Application No. PCT/JP2017/004191, filed Feb. 6, 2017, which claims priority to Japanese application No. 2016-022659 filed Feb. 9, 2016, both of which are hereby incorporated by reference in their entireties for all purposes.

TECHNICAL FIELD

The present invention relates to a method for detecting a target nucleic acid and a nucleic acid probe used therein.

BACKGROUND ART

One of methods for detecting a nucleic acid is the fluorescently labeled probe method (see Patent Literature 1 listed below). Examples of probes used in this method include nucleic acid probes having a single-strand oligonucleotide conjugated with a fluorescent dye and a quencher molecule having effect that quenches fluorescence from the fluorescent dye (also referred to as "quenching effect") in the vicinity. These nucleic acid probes are designed to hybridize with a nucleic acid that is a target (hereinafter referred to as the "target nucleic acid"). In polymerase chain reaction (hereinafter also referred to as the "PCR"), hybridization of such a nucleic acid probe with a target nucleic acid and degradation of the nucleic acid probe with a polymerase having nuclease activity results in the separation of the quencher molecule and the fluorescent dye and therefore increase in fluorescence intensity of the fluorescent dye. In this method using a nucleic acid probe having single-strand oligonucleotide, the target nucleic acid is detected by the change of fluorescence intensity or fluorescence wavelength between before and after the degradation of the nucleic acid probe.

The probes used in the fluorescently labeled probe method include nucleic acid probes having 2 oligonucleotides different in length (see Patent Literature 2 to 3 listed below). In these nucleic acid probes, 2 oligonucleotides have nucleotide sequences complementary to each other and one of the oligonucleotides is conjugated with a fluorescent dye and the other oligonucleotide is conjugated with a quencher molecule having effect that quenches the fluorescence from the fluorescent dye. In PCR, increase in temperature results m the separation of the 2 oligonucleotides. This results in the separation of the quencher molecule and the fluorescent dye and therefore increase in fluorescence intensity. Subsequent decrease in temperature results in the hybridization of the longer oligonucleotide with the target nucleic acid, allowing continued observation of fluorescence from the fluorescent dye. If no target nucleic acid is present, then decrease in temperature results in hybridization between the 2 oligonucleotides, which brings a quencher molecule near the fluorescent dye and therefore quenches fluorescence from the fluorescent dye. In this method using a nucleic acid probe having the 2 oligonucleotides, the target nucleic acid is detected by measuring the fluorescence intensity during annealing stage in the PER.

The probe used in the fluorescently labeled probe method also include Quenching Probe (hereinafter, referred to as "QProbe") labelled with a fluorescent dye that decreases its fluorescence intensity (also referred to as "quenching") when a guanine base comes in close vicinity (see Patent Literature 4 listed below). This QProbe has, at its terminal, a cytosine base conjugated with the fluorescent dye and is designed such that, when QProbe hybridizes with a target nucleic acid, this cytosine base forms a base pair with a guanine base in the target nucleic acid and the guanine base is placed in the vicinity of the fluorescent dye. Therefore, when QProbe is hybridized with the target nucleic acid, the fluorescent dye is placed in the vicinity of the guanine base and thereby quenched. In the method for detecting a nucleic acid using QProbe, the target nucleic acid is quantified by decrease in fluorescence intensity from before to after hybridization.

CITATION LIST

Patent Literature

Patent Literature 1: Japanese Unexamined Patent Publication No. H6-500021
Patent Literature 2: Japanese Unexamined Patent Publication No H1:0-262700
Patent Literature 3: Japanese Unexamined Patent Publication No. 2004-511227
Patent Literature 4: Japanese Unexamined Patent Publication No 2001-286300

SUMMARY OF INVENTION

Technical Problem

The detection of a target nucleic acid using nucleic acid probes described in Patent Literature 1 to 3 requires expensive precision instruments for the detection and takes a high cost. Furthermore, the detection of a target nucleic acid using nucleic acid probes described in Patent Literature 1 to 3 is a complex process with a large number of steps and requires skills for the detection.

Moreover, examinations by the present inventors have revealed that even the detection with QProbe has room for improvement in terms of sensitivity: for example, there are cases where it is difficult to detect the target nucleic acid with high sensitivity.

More specifically, if there is a guanine base within 1 to 7 bases from the cytosine base conjugated with the fluorescent dye QProbe, the fluorescence intensity of the fluorescent dye is decreased by the interaction with the guanine base. Thus, the fluorescence intensity of the fluorescent dye decreases even without the hybridization of QProbe with a target nucleic acid. This reduces the ratio of decrease in fluorescence intensity from the fluorescent dye from before to after the hybridization and lowers the sensitivity.

Therefore, when designing QProbe, a region suitable for hybridizing QProbe, that is, a region containing no cytosine base within 1 to 7 bases from a guanine base facing the cytosine base conjugated with the fluorescent dye for keeping high sensitivity has to be selected for the region in the target nucleic acid to which a nucleic acid probe hybridizes (hereinafter, referred to as the "probe-binding region").

The present invention has been made in view of such circumstances and an object of the present invention is to provide means for selecting a probe-binding region without limitation and allowing detection with high sensitivity. More specifically, an object of the present invention is to provide a nucleic acid probe that exhibits excellent sensitivity even when the probe-binding region of its target nucleic acid has a cytosine base within 1 to 7 bases from a guanine base facing the cytosine base conjugated with the fluorescent dye on the probe. Another object of the present invention is to provide a method for detecting a target nucleic acid using the nucleic acid probe.

Solution to Problem

To achieve the aforementioned objects, the present invention provides a first nucleic acid probe for detecting a target nucleic acid, wherein the target nucleic acid comprises a probe-binding region with which the first nucleic acid probe hybridizes; at least one terminal of the probe-binding region is a guanine base, and one or more cytosine bases are present within 1 to 7 bases from the guanine base in the probe-binding region; the first nucleic acid probe comprises an oligonucleotide having a cytosine base facing the guanine base on a terminal and a fluorescent dye conjugated to the cytosine base; the fluorescent dye is a fluorescent dye that is quenched by the interaction with a guanine base; the oligonucleotide is complementary to the nucleic acid in the probe-binding region except the cytosine base present within 1 to 7 bases from the terminal guanine base; one or more bases in the oligonucleotide facing the one or more cytosine bases is a guanine base or a base having no fluorescence-quenching effect; provided that the base in the oligonucleotide facing the cytosine base closest to the terminal guanine base among the one or more cytosine bases is a base having no fluorescence-quenching effect.

In the first nucleic acid probe, the base having no fluorescence-quenching effect is preferably a base selected from hypoxanthine, adenine, thymine, cytosine, and nebularine and more preferably a hypoxanthine base.

The present invention also provides a method for detecting a target nucleic acid, comprising the steps of: mixing the first nucleic acid probe and a sample to prepare a mixture; measuring fluorescence intensity from the mixture; and detecting, the target nucleic acid based on the fluorescence intensity.

In the method for detecting a target nucleic acid, the detection may be carried out by melting curve analysis.

The present invention also provides a method for detecting a target nucleic acid, comprising the steps of: mixing the second nucleic acid probe and a sample comprising a test nucleic acid to prepare a mixture; and conducting nucleic acid amplification reaction using the test nucleic acid contained in the mixture as a template to obtain an amplified product. The amplification reaction is a polymerase chain reaction comprising repeated cycles of a denaturation stage, an annealing stage, and an extension stage. The amplification reaction comprises, in the annealing, stage, measuring fluorescence intensity from the mixture; and detecting the target nucleic acid based on the fluorescence intensity.

The present invention also provides a second nucleic acid probe for detecting a target nucleic acid, wherein the target nucleic acid comprises a probe-binding region with which the second nucleic acid probe hybridizes; at least one terminal of the probe-binding region is a guanine base, and one or more single nucleotide polymorphisms are present within 1 to 7 bases from the guanine base in the probe-binding region; the second nucleic acid probe comprises an oligonucleotide having a cytosine base facing the guanine base on a terminal and a fluorescent dye conjugated to the cytosine base; the fluorescent dye is a fluorescent dye that is quenched by the interaction with a guanine base; the oligonucleotide is complementary to the nucleic acid in the probe-binding region except the one or more single nucleotide polymorphisms present within 1 to 7 bases from the terminal guanine base; one or more bases in the oligonucleotide facing the one or more single nucleotide polymorphisms are a guanine base or a base having no fluorescence-quenching effect; provided that the base in the oligonucleotide facing the single nucleotide polymorphism closest to the terminal guanine base among the one or more single nucleotide polymorphisms is a base having no fluorescence-quenching effect.

In the second nucleic acid probe, the base having no fluorescence-quenching effect is preferably a base selected from hypoxanthine, adenine, thymine, cytosine, and nebularine and more preferably a hypoxanthine base.

The present invention also provides a method for detecting a target nucleic acid, comprising the steps of: mixing the second nucleic acid probe and a sample to prepare a mixture; measuring fluorescence intensity from the mixture; and detecting the target nucleic acid based on the fluorescence intensity. This detection may be conducted by melting curve analysis and the single nucleotide polymorphism may be detected by melting curve analysis.

The sample may comprise an amplified product obtained by a nucleic acid amplification reaction using a test nucleic acid as a template.

Advantageous Effects of Invention

According to the present invention, if at least one terminal of the probe-binding region in the target nucleic acid is a guanine base, then the probe-binding region can be selected without limitation and QProbe that allows high sensitive detection can be designed. More specifically, the present invention can provide a nucleic acid probe (first nucleic acid probe) that exhibits excellent sensitivity even when the probe-binding region of its target nucleic acid has a cytosine base within 1 to 7 bases from a guanine base facing the cytosine base conjugated with the fluorescent dye on the probe.

According to the present invention, a method for detecting a target nucleic acid using the nucleic acid probe (first nucleic acid probe) can also be provided.

According to the present invention, a nucleic acid probe (second nucleic acid probe) that allows the detection of single nucleotide polymorphism (SNP) can also be provided.

According to the present invention, a method for detecting a target nucleic acid using the nucleic acid probe (second nucleic acid probe) can also be provided.

BRIEF DESCRIPTION OF DRAWINGS

FIGS. 1(a) and 1(b) are schematic diagrams illustrating the mechanism of the nucleic acid detection with the first nucleic acid probe according to the present invention.

FIGS. 8(a) to 8(e) illustrate results of detection of single nucleotide polymorphism (SNP).

DESCRIPTION OF EMBODIMENTS

Figure 2:
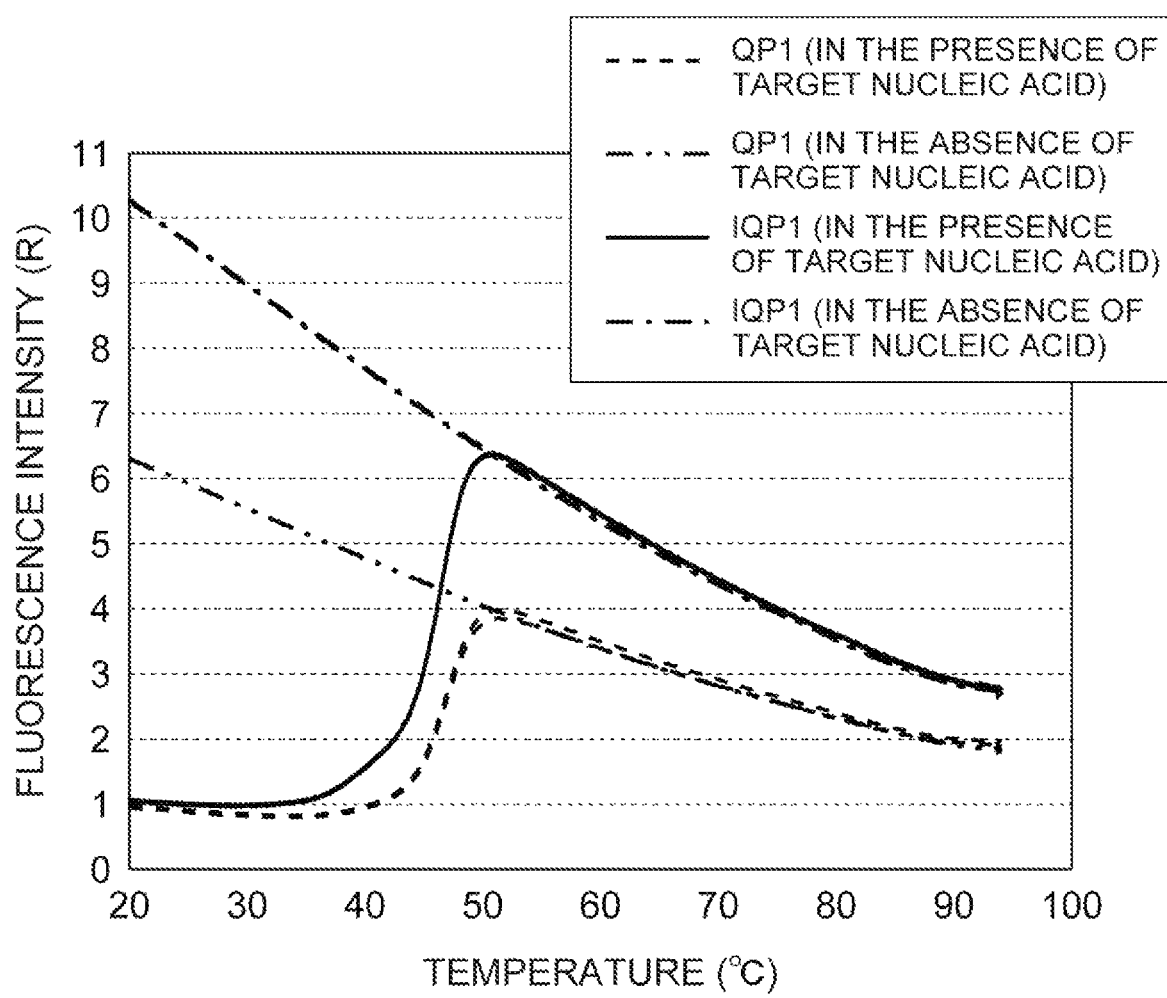
FIG. 2 illustrates a result of the inciting curve analysis performed with a nucleic acid probe having a nucleotide sequence with a substitution of a guanine base adjacent to the cytosine base present at a terminal of the oligonucleotide with a hypoxanthine base.

A preferred embodiment of the present invention will be described below referring to a drawing(s), if needed.

The term "target nucleic acid" as used herein refers to a nucleic acid of interest to be detected with a probe described in the present embodiment.

The term "complementary" as used herein means that adenine and thymine bases or guanine and cytosine bases can make pairs and form hydrogen bonds.

The term "single nucleotide polymorphism (SNP)" as used herein refers to polymorphism caused by substitution of a single nucleotide in a nucleotide sequence.

The term "perfect match" as used herein means that the nucleotide sequence of oligonucleotide in a probe is fully complementary to the nucleotide sequence of the probe-binding region in the target nucleic acid and the probe-binding region in the target nucleic acid and the oligonucleotide in the probe hybridize with each other.

Meanwhile, the term "mismatch" as used herein means that the nucleotide sequence of oligonucleotide in the probe has one or more bases that is not complementary to the nucleotide sequence of the probe-binding region in the target nucleic acid and therefore the probe-binding region in the target nucleic acid and the oligonucleotide in the probe cannot hybridize with each other or their hybrid has a melting temperature lower than that of "perfect match".

The term "melting temperature" as used herein means the temperature at which 50% of the double strand nucleic acid is denatured and present as single strand nucleic acid.

The source of the target nucleic acid is not particularly limited and the target nucleic acid may be a nucleic acid derived from an animal, a plant, a fungus, a microorganism, or a virus.

The nucleic acid in the present embodiment may be a naturally occurring DNA or RNA or an artificial nucleic; acid such as Locked Nucleic Acid (LNA) and Peptide Nucleic Acid (PNA).

The target nucleic; acid in the present embodiment comprises a probe-binding region with which the first nucleic acid probe hybridizes.

At least one terminal (which may be the 5 terminal or the 3' terminal) of the probe-binding region in the target nucleic acid is a guanine base.

One or more cytosine bases are present within 1 to 7 bases from a guanine base in the probe-binding region, the guanine base located at a terminal of the probe-binding region in the target nucleic acid. The cytosine base may be within 5 bases or within 3 bases from the guanine base located at the terminal of the probe-binding region or a base adjacent to the terminal guanine base may be a cytosine base from the viewpoint that the first nucleic acid probe in the present embodiment exhibits superior sensitivity when a guanine base facing such a cytosine base was substituted with a base having no fluorescence-quenching effect.

The first nucleic acid probe according to the present embodiment comprises an oligonucleotide having, at a terminal, a cytosine base facing a guanine base located at a terminal of the probe-binding region and a fluorescent dye conjugated with the cytosine base and quenched by a guanine base.

The oligonucleotide in the first nucleic acid probe is perfectly complementary with the nucleic acid in the probe-binding region, except the one or more cytosine bases present within 1 to 7 bases from the terminal guanine base in the probe-binding region. A base in the oligonucleotide facing the one or more cytosine bases is a guanine base or a base having no fluorescence-quenching effect provided that the base in the oligonucleotide facing the cytosine base closest to the terminal guanine base in the probe-binding region among the one or more cytosine bases is a base having no fluorescence-quenching effect.

When 2 or more guanine bases are present within 1 to 7 bases from the cytosine base at the terminal, one or more guanine bases other than the guanine base located closest to the cytosine base at the terminal may be substituted with a base having no fluorescence-quenching effect or not substituted. From the viewpoint of increasing the sensitivity of the first nucleic acid probe more, it is preferred that 2 or more bases among the guanine bases present within 1 to 7 bases from the cytosine base at the terminal are substituted with those having no fluorescence-quenching effect.

The term "base having no fluorescence-quenching effect" as used herein refers to a base that, when located near a fluorescent dye that is quenched by the interaction with a guanine base, does not quench fluorescence of the fluorescent dye or a base that reduces the fluorescence intensity of the fluorescent dye less than a guanine base.

The base having no fluorescence-quenching effect is preferably a base selected from hypoxanthine, adenine, thymine, cytosine, and nebularine from the viewpoint of good sensitivity. Furthermore, the base having no fluorescence-quenching effect is more preferably a hypoxanthine base. Since the hypoxanthine base can form a hydrogen bond with a cytosine base, if the base having no fluorescence-quenching effect is a hypoxanthine base, then it allows strong binding of the first nucleic acid probe to the probe-binding region in the target nucleic acid.

The fluorescent dye contained in the first nucleic acid probe is quenched by the interaction with a guanine base. More specifically, if there is a guanine base in the vicinity of the fluorescent dye, then fluorescence resonance energy transfer occurs and the fluorescence intensity decreases. Examples of such a fluorescent dye include fluoresceine or derivatives thereof (fluorescein isothiocyanate (FITC)), tetramethylrhodamine (TMR), 6-JOE, AlexaFluor (R) 488 (Molecular Probes), Cy (R) 3 (GE Healthcare), Cy (R) 5 (GE Healthcare), BODIPY (R)-FL (Molecular Probes), and carboxy tetramethylrhodamine (TAM).

The oligonucleotide in the first nucleic acid probe according to the present embodiment may be an oligonucleotide obtained by an ordinal method of producing an oligonucleotide. Examples of such an oligonucleotide include oligonucleotides obtained by chemical synthesis. In the chemical synthetic method, any bases such as adenine, cytosine, guanine, thymine, hypoxanthine, or nebularine can be introduced into any position.

A fluorescent dye can be conjugated with an oligonucleotide according to a conventionally known method (see, for example, Patent Literature 4 listed above).

When the fluorescent dye is conjugated with the 5' terminal of the oligonucleotide, examples of such a method include a method involving inducing a thiol group at the 5' terminal phosphate group of the oligonucleotide and covalently bonding a fluorescent dye to this thiol group.

When the fluorescent dye is conjugated with the 3' terminal of the oligonucleotide, examples of such a method include a method introducing an amino group into a hydroxy group bound to the 3' carbon atom of the ribose or deoxyribose and covalently bonding a fluorescent dye to this amino group.

The first nucleic acid probe in the present embodiment allows the detection of a target nucleic acid based on change in fluorescence intensity even when a cytosine base is present within 1 to 7 bases from the guanine base, in the probe-binding region in the target nucleic acid, facing the cytosine base conjugated with the fluorescent dye.

An example of the embodiment of the method for detecting a target nucleic acid is a method comprising mixing the first nucleic acid probe in the present embodiment and a sample to prepare a mixture; measuring fluorescence intensity from the mixture; and detecting the target nucleic acid based on the fluorescence intensity.

FIGS. 1(a) and 1(b) schematically illustrate a first nucleic acid probe in the present embodiment and a nucleic acid to be detected. When a nucleic acid has a probe-binding region, the first nucleic acid probe hybridizes with the probe-binding region in the nucleic acid. Upon the hybridization, the fluorescence from the fluorescent dye is quenched by the fluorescent dye conjugated with the cytosine base present at a terminal of the first nucleic acid probe coming in the vicinity of the guanine base present in the probe-binding region in the nucleic acid (FIG. 1(a)).

Meanwhile, when a nucleic acid does not have a probe-binding region, the fluorescence of the fluorescent dye is not quenched since the nucleic acid cannot hybridize with the first nucleic acid probe and no guanine base comes in the vicinity of the fluorescent dye. Thus, the fluorescence of the fluorescent dye is observed in this case (FIG. 1 (b)).

Therefore, for example, if the fluorescence intensity is decreased after mixing the first nucleic acid probe according to the present embodiment and a sample, in comparison with that before mixing, then it can be determined that the target nucleic acid is present in the sample.

Another embodiment of the method for detecting a target nucleic acid includes a method involving performing the melting curve analysis. The melting curve analysis can be performed by a conventionally known method (see, for example, Patent Literature 1 listed above).

An example of the melting curve analysis is the following method. In this method, the first nucleic acid probe according to the present embodiment and a sample are mixed and double strand nucleic acid in the sample is dissociated (denatured) into single strand nucleic acid by heating. Furthermore; in this method, the fluorescence intensity from the mixture is measured while decreasing the temperature of this mixture to a temperature (hereinafter, referred to as the "hybridization temperature" in some cases) at which the first nucleic acid probe and the target nucleic acid hybridize with each other.

If the nucleic acid in the sample has a probe-binding region, then decreasing the temperature of the mixture to a predetermined temperature causes the hybridization of the first nucleic acid probe to the nucleic acid in the sample, which brings a guanine base in the vicinity of the fluorescent dye and therefore decreases the fluorescence intensity from the mixture. Hereinafter, the temperature at this time is referred to as the "quenching initiation temperature".

Meanwhile, if the nucleic acid in the sample does not have a probe-binding region, then, even when the temperature is decreased to a quenching initiation temperature, the nucleic acid in the sample cannot hybridize with the first nucleic acid probe and no guanine base comes in the vicinity of the fluorescent dye and therefore the fluorescence intensity from the mixture does not decrease.

Therefore, if the fluorescence intensity from the mixture observed when the temperature of the mixture is decreased to the hybridization temperature is decreased in comparison with the fluorescence intensity observed at a quenching initiation temperature, then it can be determined that the target nucleic acid is present in the sample.

The sample may comprise an amplified product obtained by a nucleic acid amplification reaction using a test nucleic acid as a template.

Examples of another embodiment of the method for detecting a target nucleic acid include a method comprising mixing the first nucleic acid probe according to the present embodiment and a sample comprising the test nucleic acid to prepare a mixture; and conducting nucleic acid amplification reaction using the test nucleic acid contained in the mixture as a template to obtain an amplified product. The amplification reaction is a polymerase chain reaction comprising repeated cycles of a denaturation stage, an annealing stage, and an extension stage. The amplification reaction comprises, in the annealing stage, measuring fluorescence intensity from the mixture; and detecting the target nucleic acid based on the fluorescence intensity.

In the nucleic acid amplification reaction, if the target nucleic acid has a probe-binding region, then the first nucleic acid probe hybridizes with the probe-binding region in the nucleic acid in the annealing stage. Upon the hybridization, the fluorescent dye on the first nucleic acid probe comes in the vicinity of the terminal guanine base in the probe-binding region and thereby the fluorescence from the fluorescent dye is quenched.

Increasing the repeating number of cycles of nucleic acid amplification reaction increases the target nucleic acid (amplified product) in the sample and therefore increases the first nucleic acid probe that hybridizes with the target nucleic acid, in the annealing stage. Therefore, when the fluorescence intensity from the mixture is measured in the annealing stage in the nucleic acid amplification reaction, the decrease in fluorescence intensity increases with the increase of the repeating number of cycles of the nucleic acid amplification reaction.

The nucleic acid amplification reaction may be Loop-mediated Isothermal Amplification (LAMP). Specific examples of another embodiment of the method for detecting a target nucleic acid includes a method comprising mixing the first nucleic acid probe according to the present embodiment and a sample containing a test nucleic acid to prepare a mixture; and conducting nucleic acid amplification, reaction (LAMP) using the test nucleic acid contained in the mixture as a template to obtain an amplified product.

The second nucleic acid probe will be described. The second nucleic acid probe has a configuration similar to the first nucleic acid probe except that one or more single nucleotide polymorphisms are present within 1 to 7 bases from the terminal guanine base in the probe-binding region; and the oligonucleotide in the second nucleic acid probe is complementary to the nucleic acid in the probe-binding region except the one or more single nucleotide polymorphisms within 1 to 7 bases from the terminal guanine base; a base in the oligonucleotide facing the one or more single nucleotide polymorphisms is a guanine base or a base having no fluorescence-quenching effect; and the base in the oligonucleotide facing the single nucleotide polymorphism closest to the terminal guanine base among the one or more single nucleotide polymorphisms is a base having no fluorescence-quenching effect. More specifically, the second nucleic acid probe is one modified from the first nucleic acid probe by substituting the base in the oligonucleotide facing the "single nucleotide polymorphism" present within 1 to 7 bases from the terminal guanine base in the probe-binding region with a base having no fluorescence-quenching effect.

The detection of the SNP is possible by the melting curve analysis using the second nucleic acid probe.

When a probe is hybridized with a target nucleic acid, the quenching initiation temperature varies depending on the kind of the base in the probe-binding region facing the base having no fluorescence-quenching effect in the probe.

Therefore, the presence or absence of SNP and the kind of base constituting the SNP can be determined, for example, as follows. First, the quenching initiation temperature when the kind of the base in the probe-binding region facing the base having no fluorescence-quenching effect in the probe was changed into another base is measured beforehand. Next, the presence or absence of SNP and the kind of base constituting the SNP can be determined by comparing the quenching initiation temperature measured beforehand and the quenching initiation temperature of the target nucleic acid in the sample measured separately.

EXAMPLES

The present invention will be more specifically described by Examples below, but the present invention is not limited by these Examples,

[Example 1] Melting Curve Analysis Using QProbe with Hypoxanthine Base Substitution In an oligonucleotide in a nucleic acid probe, the melting curve analysis was performed using QProbe in which a guanine base locating 1 base apart from a cytosine base conjugated with a fluorescent dye is substituted with a hypoxanthine base (hereinafter, referred to as "IQP1"). Moreover, the melting curve analysis using QProbe with no substitution (hereinafter, referred to as "QP1") was performed as Comparative Example.

(Materials)
Target nucleic acid: synthetic DNA having the nucleotide sequence set forth in SEQ ID NO: 1 (hereinafter, also referred to, as "Model 1"), 10 μM.

QProbes: probes comprising oligonucleotides having a nucleotide sequence set forth in SEQ ID NO: 2 or 3 and conjugated with TAMRA at a terminal cytosine base in the oligonucleotide (QP1 and IQP1), 2 μM.

Hybridization buffer: a buffer containing KCl, Tris-HCl (pH 8.0), and TWEEN-20™ (polyoxyethylene (20) sorbitan monostearate).

The target nucleic acid and QProbes were synthesized by Japan Bio Services Co., LTD by request.

Details of Model 1, QP1, and IQP1 are set forth in Table 1. A hypoxanthine base is represented by I in the nucleotide sequence.

TABLE 2

| Name | | SEQ ID NO: | Base sequence | Base type after substitution |
|---|---|---|---|---|
| Target nucleic acid | Model 1 | 1 | GCTTTTTTTTTTT TTTTTTC | — |
| QProbe | QP1 | 2 | AAAAAAAAAAAA AAAAAGC | — |
|  | IQP1 | 3 | GAAAAAAAAAAAA AAAAAAIC | Hypoxanthine |

(Method)
3.2 μL, of Model 1, 0.5 μL of QP1 or IQP1, and 21.3 μL of the hybridization buffer were mixed and a mixture containing 1.28 μm Model 1, 0.04 μMQP1 or IQP1, 50 mM KCl, 10 mM Tris-HCl (pH 8.0), and 0.1% TWEEN-20™ (polyoxyethylene (20) sorbitan monostearate) at final concentrations was prepared. In addition, 0.5 μL of QP1 or IQP1 and 24.5 μL of hybridization buffer, but not Model 1, were mixed to prepare a mixture. The preparation of mixtures was performed in octuplicate tubes. The melting curve analysis was performed by measuring fluorescence intensity while lowering the temperature of the mixture from 95° C. to 20° C. The temperature was lowered at −0.06° C./s and the measurement was conducted five times for every degree Celsius. The measurement was conducted for fluorescence intensity at 520 nm, using LightCycler (R) 480 Instrument II (F. Hoffmann-La Roche Ltd) with an excitation wavelength of 533 nm.

The same measurement was performed twice.
(Result)
When using IQP1, as well as QP1, fluorescence was quenched under a certain temperature when Model 1 was present in the mixture, while quenching was not observed when no Model 1 was present in the mixture (FIG. 2).

Moreover, when using IQP1, the fluorescence intensity at the quenching initiation point (hereinafter, also referred to as "peak point") was greater than that when using QP1. More specifically, when using IQP1, the difference (decrease) between the fluorescence intensity at the peak point and the fluorescence intensity at the time when decrease in fluorescence intensity with decrease in temperature of the mixture ended to be observed and the fluorescence intensity reached a plateau was greater than that when using QP1.

The result of Example 1 indicated that IQP1 is quenched in the presence of a target nucleic acid in a mixture and it is possible to detect the target nucleic acid. IQP1 was also shown to be more sensitive than QP1.

[Example 2] Melting Curve Analysis Using QProbe with Various Base Substitutions

Melting curve analysis was performed using QProbe in which a guanine base adjacent to the cytosine base conjugated with a fluorescent dye is substituted with a base selected from hypoxanthine, thymine, cytosine, adenine, nebularine, 2-dimethylaminomethyleneamino-6-methoxyaminopurine, and 3-nitropyrrole (hereinafter, referred to as "IQP1", "TQP", "CQP", "AQP", "NQP", "dKQP", or "NitQP", respectively).

(Materials)
Target nucleic acid: Model 1, 10 μM.
QProbes: probes comprising oligonucleotides having a nucleotide sequence set forth in SEQ ID NO: 2 to 9 and conjugated with TAMRA at a terminal cytosine base in the oligonucleotide (QP1, IQP1, TQP, CQP, AQP, NQP, dKQP, and NitQP), 2 µM.

Hybridization buffer: a buffer containing KCl, Tris-HCl (pH 8.0), and TWEEN-20™ (polyoxyethylene (20) sorbitan monostearate).

The target nucleic acid and QProbes were synthesized by Japan Bio Services Co., LTD by request.

Details of Model 1, QP1, IQP1, TQP, CQP, AQP, NQP, dKQP, and NitQP are set forth in Table 2. Hereinafter, bases after substitution of a guanine base adjacent to the cytosine base conjugated with a fluorescent dye with thymine, cytosine, adenine, nebularine, 2-dimethylaminomethyleneamino-6-methoxyaminopurine, and 3-nitropyrrole are in some cases represented by T, C, A, N, dK, and Nit, respectively.

TABLE 2

| | Name | SEQ ID NO | Base sequence (5'-3') | Base type after substitution |
|---|---|---|---|---|
| Target nucleic acid | Model 1 | 1 | GCTTTTTTTTTTTTTTTTC | — |
| QProbe | QP1 | 2 | AAAAAAAAAAAAAAAAAGC | — |
| | IQP1 | 3 | GAAAAAAAAAAAAAAAAA<u>I</u>C | Hypoxanthine |
| | TQP | 4 | GAAAAAAAAAAAAAAAAA<u>T</u>C | Thymine |
| | CQP | 5 | GAAAAAAAAAAAAAAAAA<u>C</u>C | Cytosine |
| | AQP | 6 | GAAAAAAAAAAAAAAAAA<u>A</u>C | Adenine |
| | NQP | 7 | GAAAAAAAAAAAAAAAAA<u>N</u>C | Nebularine |
| | dKQP | 8 | GAAAAAAAAAAAAAAAAA<u>dK</u>C | 2-Dimethyl-amino-methylene-amino-6-methoxy aminopurine |
| | NitQP | 9 | GAAAAAAAAAAAAAAAAA<u>Nit</u>C | 3-Nitropyrrole |

(Method)

Melting curve analysis was performed by a method similar to Example 1 except that TQP, CQP, AQP, NQP, DKQP, and NitQP were used and the mixtures composed of respective QProbes and the hybridization buffer were not prepared.

(Result)

Figure 3:
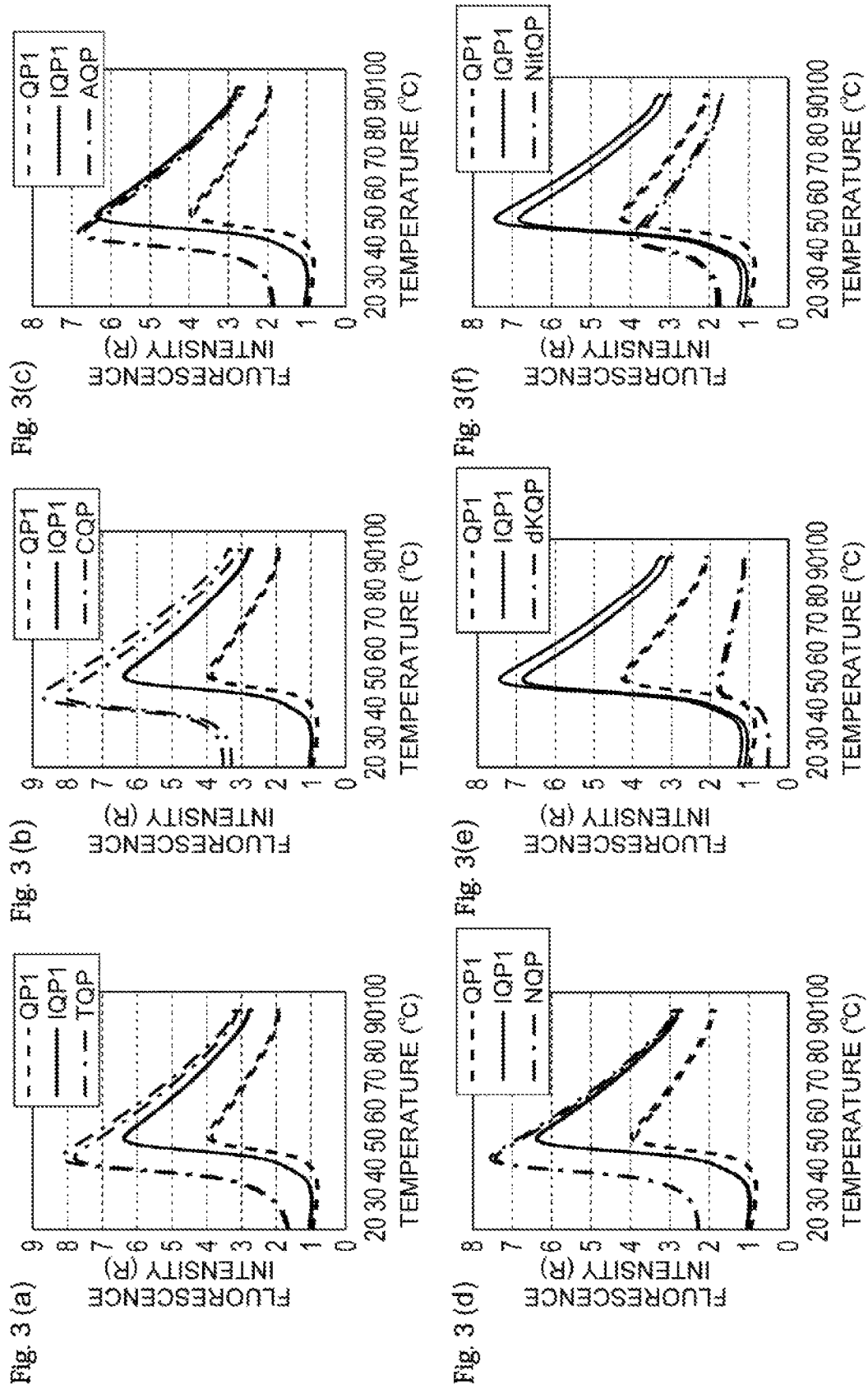
FIGS. 3(a) to 3(f) illustrate results of the melting curve analysis performed with a nucleic acid probe having a nucleotide sequence with a substitution of a guanine base adjacent to the cytosine base present at a terminal of the oligonucleotide with other base such as a thymine base.
Figure 4:
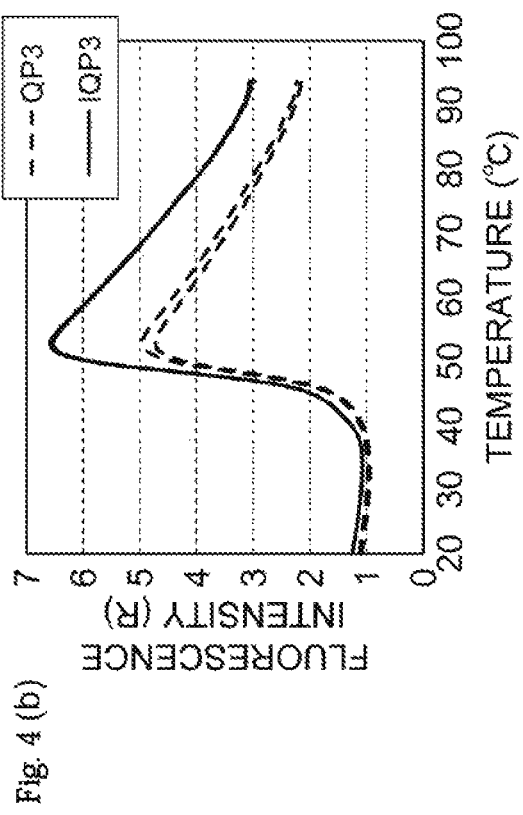
FIGS. 4(a) to 4(d) illustrate results of the melting curve analysis performed with probes having stepwisely varying distances between with a guanine base to be substituted with a hypoxanthine base and a cytosine base conjugated with a fluorescent dye.
Figure 4:
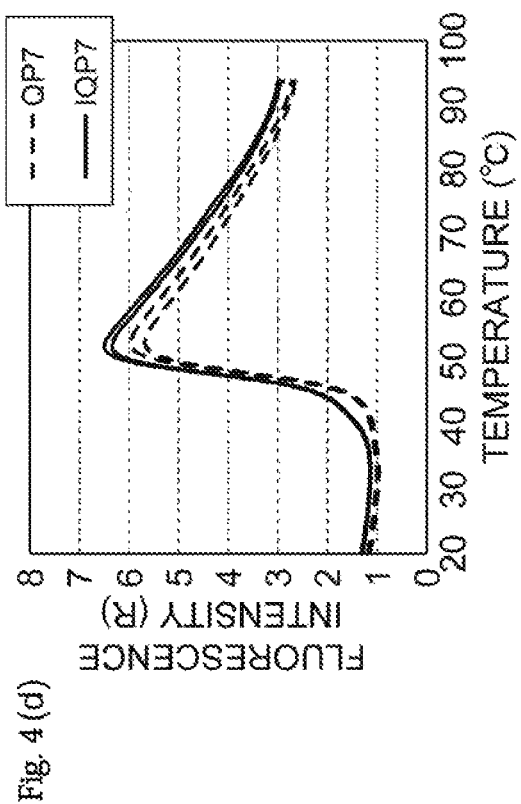
Figure 4C:
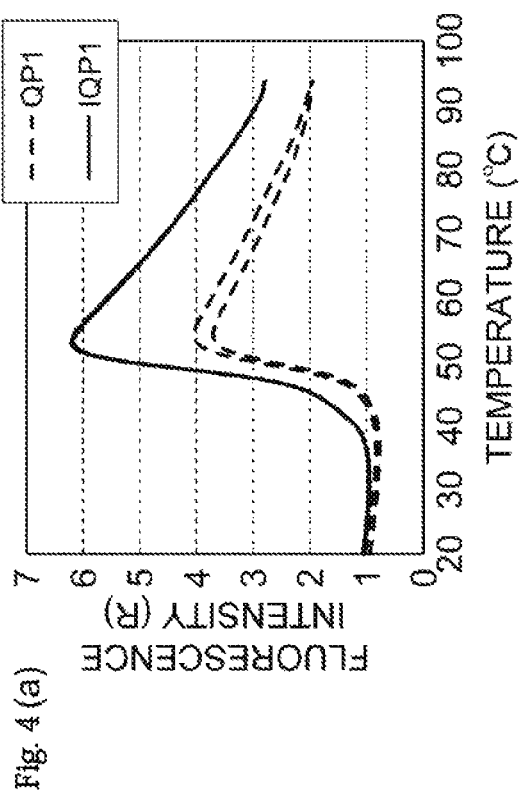
Figure 4:
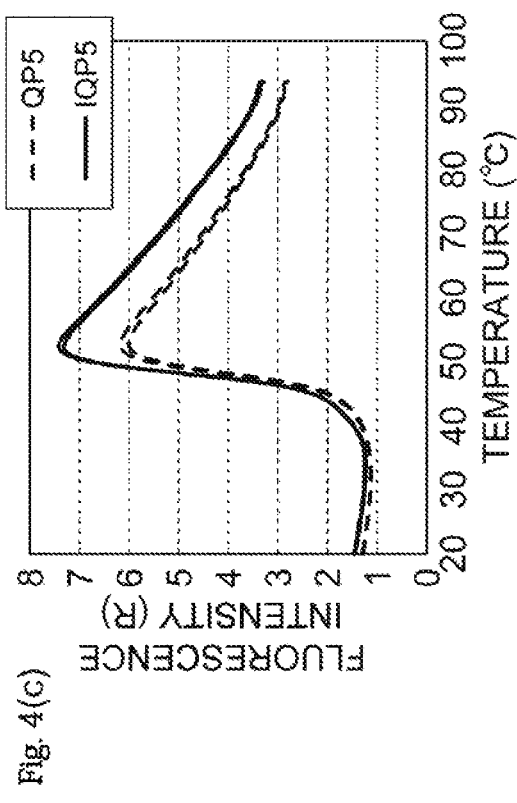

When using a QProhe selected from IQP1, TQP, CQP, AQP, and NQP, the fluorescence intensity at the peak point was increased in comparison with that when using QP1 FIGS. 3 (a) to 3(d)). More specifically, when using a QProhe selected from IQP1, TQP, CQP, AQP, and NQP, the difference (decrease) between the fluorescence intensity at the peak point and the fluorescence intensity at the time when decrease in fluorescence intensity with decrease in temperature of the mixture ended to be observed and the fluorescence intensity reached a plateau was, greater than that when using QP1.

The result of Example 2 indicated that IQP1 TQP, CQP, AQP, and NQP are more sensitive than QP1.

[Example 3] Selection of Position to be Substituted

The melting curve analysis was performed with Qprobes having stepwisely varying distances between a guanine base to be substituted with a hypoxanthine base and a cytosine base conjugated with a fluorescent dye. Specifically, melting curve analysis was performed using synthetic DNAs having the nucleotide sequences set forth in SEQ ID NOs: 1 and 10 to 12 (hereinafter, referred to as "Model 1", "Model 2", "Model 3", and "Model 4", respectively) as target nucleic acids and using (Probes in which an guanine base 1, 3, 5, or 7 bases apart from the cytosine base conjugated with a fluorescent dye is substituted with a hypoxanthine base (hereinafter, referred to as "IQP1", "IQP3", "IQP5", and "IQP7", respectively). Moreover, the melting curve analysis using QProbes with, no substitution (hereinafter, referred to as "QP1", "QP3", "QP5", and "QP7", respectively) was performed as Comparative Examples.

(Materials)

Target nucleic acid: DNAs having the nucleotide sequences set forth in SEQ ID NOs: 1 and 10 to 12 (Models 1 to 4), 10 µM.

QProbe: Probes comprising oligonucleotides having the nucleotide sequences set forth in SEQ ID NO: 2, 3, and 13 to 18 and conjugated with TAMRA at a terminal cytosine base in the oligonucleotides (QP1, QP3, QP5, QP7, IQP1, IQP3, IQP5, and IQP7), 2 µM.

Hybridization buffer: a buffer containing KCl, Tris-HCl (pH 8.0), and TWEEN-20™ (polyoxyethylene (20) sorbitan monostearate).

The target nucleic acid and QProbes were synthesized by Japan Bio Services Co., LTD by request.

Details of Models 1 to 4, QP1, QP3, QP5, QP7, IQP1, IQP3, IQP5, and IQP7 are set forth in Table 3.

TABLE 3

| | Name | SEQ ID NO | Base sequence (5'-3') | Distance (bases) from cytosine base conjugated with fluorescent dye to hypoxanthine base |
|---|---|---|---|---|
| Target nucleic acid | Model 1 | 1 | GCTTTTTTTTTTTTTTTTC | — |
| | Model 2 | 10 | GTTCTTTTTTTTTTTTTTC | — |
| | Model 3 | 11 | GTTTTCTTTTTTTTTTTTC | — |
| | Model 4 | 12 | GTTTTTTCTTTTTTTTTTC | — |
| QProbe | QP1 | 2 | AAAAAAAAAAAAAAAAAGC | — |
| | QP3 | 13 | AAAAAAAAAAAAAAAGAAC | — |
| | QP5 | 14 | AAAAAAAAAAAAAGAAAAC | — |
| | QP7 | 15 | AAAAAAAAAAAGAAAAAAC | — |
| | IQP1 | 3 | AAAAAAAAAAAAAAAAA<u>I</u>C | 1 |
| | IQP3 | 16 | GAAAAAAAAAAAAAAA<u>I</u>AAC | 3 |
| | IQP5 | 17 | GAAAAAAAAAAAAA<u>I</u>AAAAC | 5 |
| | IQ27 | 18 | GAAAAAAAAAAAA<u>I</u>AAAAAAC | 7 |

(Method)

The melting curve analysis was performed by a method similar to that of Example 2 except that Models 2 to 4, QP3, QP5, QP7, IQP3, IQP5, and IQP7 were used.

(Result)

When using QProbe having a substitution selected from IQP1, IQP3, IQP5, and IQP7, the fluorescence intensity at the quenching initiation point was increased in comparison with that when using QProbe with no substitution (FIGS. 4(a) to 4(d)). More specifically, when using QProbe having a substitution selected from IQP1, IQP3, IQP5, and IQP7, the difference (decrease) between the fluorescence intensity at the peak point and the fluorescence intensity at the time when decrease in fluorescence intensity with decrease in temperature of the mixture ended to be observed and the fluorescence intensity reached a plateau was greater than that when using QProbe having no substitution.

From the result of Example 3, IQP1, IQP3, IQP5, and IQP7 have improved sensitivity than QProbe having no substitution.

[Example 4] Melting Curve Analysis Using QProbe with Multiple Base Substitutions Melting curve analysis was performed using QProbes having substitutions of a plurality of guanine bases with hypoxanthine bases present within 1 to 7 bases from the cytosine base conjugated with a fluorescent dye. Specifically, the melting curve analysis was performed using synthetic DNA having the nucleotide sequence set forth in SEQ ID NO: 19 (hereinafter, referred to as "Model 5") as a target nucleic acid and using QProbe in which 1 or 2 guanine bases are substituted with a hypoxanthine base (hereinafter, referred to as "I1QP" and "I2QP", respectively). QProbe having the nucleotide sequence set forth in SEQ ID NO: 20 is hereinafter referred to as "2QP".

(Materials)

Target nucleic acid: Synthetic DNA having the nucleotide sequence set forth in SEQ ID NO: 19 (Model 5), 10 μM.

QProbe: Probes comprising oligonucleotides having SEQ ID NOs: 20 to 22 and conjugated with TAMRA at a terminal cytosine base in the oligonucleotides (2QP1, I1QP, and I2QP), 2 μM.

Hybridization buffer: a buffer containing KCl, Tris-HCl (pH 8.0), and TWEEN-20™ (polyoxyethylene (20) sorbitan monostearate).

The target nucleic acid and QProbes were synthesized by Japan Bio Services Co., LTD by request.

Details of Model 5 and 2QP, I1QP, and I2QP are set forth in Table 4.

TABLE 4

| Name | | SEQ ID NO: | base sequence (5'-3') | Number (bases) of guanine bases substituted with hypoxanthine base |
|---|---|---|---|---|
| Target nucleic acid | Model 5 | 19 | GCCTTTTTTTTTTTT TTTTCC | — |
| QProbe | 2QP | 20 | AAAAAAAAAAAAAAA AGGC | 0 |
| | I1QP | 91 | GAAAAAAAAAAAAAA AAGIC | 1 |
| | I2QP | 22 | GGAAAAAAAAAAAAA AAAIIC | 2 |

(Method)

Melting curve analysis was performed by a method similar to Example 2 except that 2QP, I1QP, and I2QP were used.

(Result)

Figure 5:
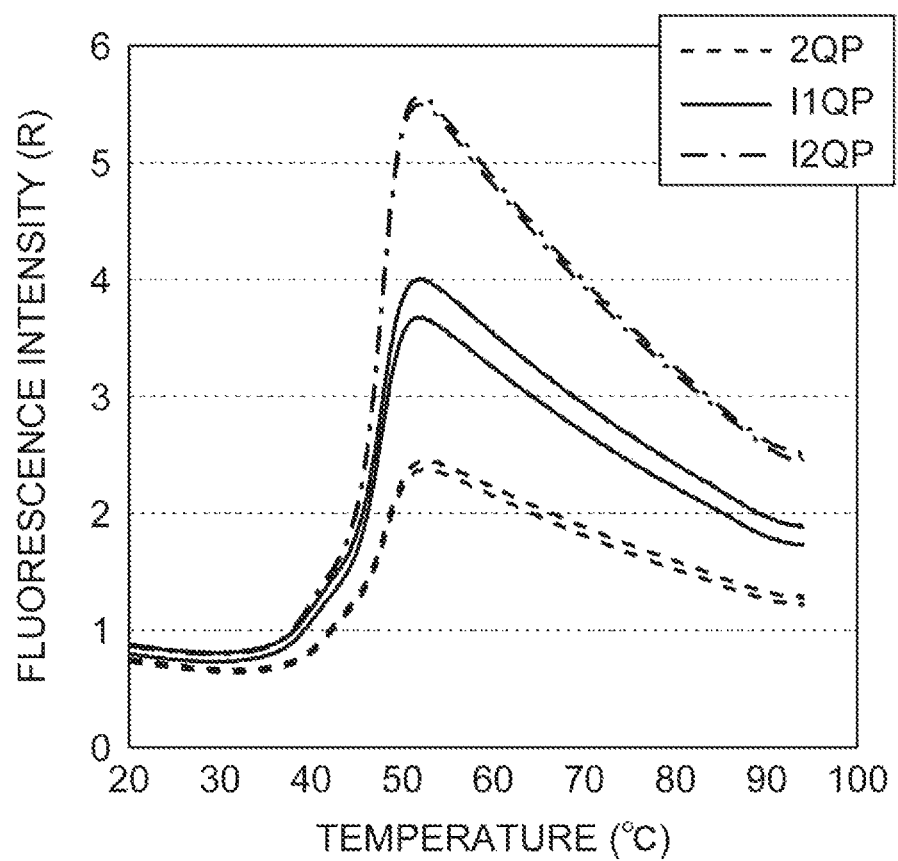
FIG. 5 illustrates a result of the melting curve analysis performed with probes having substitutions of a plurality of guanine bases with hypoxanthine bases present within 1 to 7 bases from the cytosine base conjugated with a fluorescent dye.

When using I2QP, the fluorescence intensity at the peak point is increased in comparison with that when using I1QP (FIG. 5). More specifically, when using I2QP, the difference (decrease) between the fluorescence intensity at the peak point and the fluorescence intensity at the time when decrease in fluorescence intensity with decrease in temperature of the mixture ended to be observed and the fluorescence intensity reached a plateau was greater than that when using I1QP.

The result of Example 4 indicated that the probe sensitivity is improved by substituting a plurality of guanine bases with hypoxanthine bases present within 1 to 7 bases from the cytosine base conjugated with a fluorescent dye.

[Example 5] Detection of *Mycoplasma pneumoniae* by LAMP

*Myroplasma pneumoniae* was detected by LAMP using Qprobe having substitution of a guanine base present within 1 to 7 bases from the cytosine base conjugated with a fluorescent dye with a hypoxanthine base. Specifically, LAMP was performed using purified genomic DNA from *Mycoplasma pneumoniae* strain FH having the nucleotide sequence set forth in SEQ ID NO: 23 (hereinafter, referred to as "MycP genome") as a target nucleic acid and using QProbe (hereinafter, referred to as "MycP-IQP") in which a guanine base 2 bases apart from the cytosine base conjugated with a fluorescent dye is substituted with a hypoxanthine base to detect MycP genome in real time. In addition, MycP genuine was detected using QProbe (hereinafter, referred to as "MycP-QP") with no substitution as Comparative Example.

(Materials)

Target nucleic acid: purified genomic DNA from *Mycoplasma pneumoniae* strain FH having the nucleotide sequence set forth in SEQ ID NO: 23(MycP genome).

QProbe: Probes comprising oligonucleotides having SEQ ID NO: 24 to 25 and conjugated with TAMRA at a terminal cytosine base in the oligonucleotides (MycP-QP and MycP-IQP), 2 μM.

Loopamp (R) *Mycoplasma* P Detecting Reagent Kit (reaction mix MycP (RM MycP), strand displacement DNA Polymerase (Bst Pol))

MycP genome heat-treated at 95° C. for 5 minutes and quickly cooled was used for the measurement. QProbes were synthesized by Japan Bio Services Co., LTD by request.

Details of MycP genome and MycP-QP and MycP-IQP are set forth in Table 5.

TABLE 5

| Name | | SEQ ID NO: | Base sequence (5'-3') of probe |
|---|---|---|---|
| Target nucleic acid | MycP genome | 23 | — |
| QProbe | MycP-QP | 24 | TCCGACCAAAAGGCCACCGCC |
| | MycP-IQP | 25 | GTCCGACCAAAAGGCCACCICC |

(Method)

20.00 μL of RM MycP and 1.00 μL of Bst Pot were mixed to obtain a mixture. 20.00 μL of this mixture, 0.50 μL of MycP-QP or MycP-IQP, and 4.50 μL of MycP genome were mixed to obtain 25.00 μL of a mixture containing MycP-QP or MycP-IQP at a final concentration of 0.04 μM. The mixture was incubated at 65° C. for 60 minutes and the fluorescence intensity from the mixture was measured in real time. Moreover, fluorescence intensity from the mixture obtained by mixing purified water instead of MycP genome was measured in real time in the same manner as that with MycP genome.

In the measurement, fluorescence intensity at 580 nm was measured at an excitation wavelength of 556 nm using Mx3005P (a product, made by Agilent Technologies Inc.). The software MxPro was used for the analysis. The same measurement was performed twice.

(Result)

Figure 6:
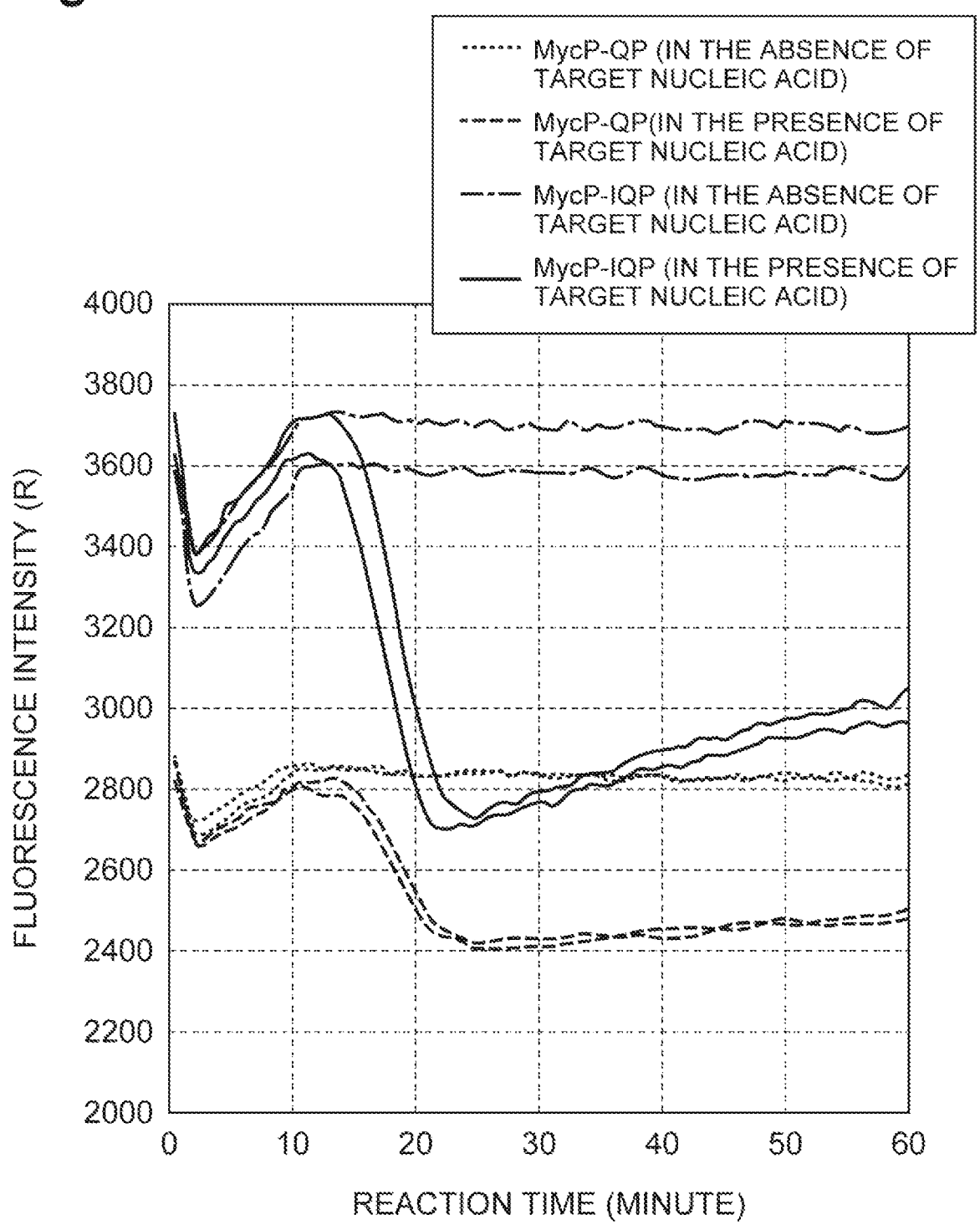
FIG. 6 illustrates a result of detection of *Mycoplasma pneumoniae* by LAMP.

In comparison of the mixture with MycP-IQP and the mixture with MycP-QP, the difference in fluorescence intensity between from the mixture containing MycP genome and from the mixture containing no Myc genome was greater with MycP-IQP than with MycP-QP (FIG. 6).

The result of Example 5 revealed that when using Qprobe having substitution of a plurality of guanine bases present within 1 to 7 bases from the cytosine base conjugated with a fluorescent dye with hypoxanthine bases, the detection of *Mycoplasma pneumoniae* by LAMP can be performed with higher sensitivity in comparison with that when using QProbe without the substitution.

[Example 6] Detection of *Mycobacterium tuberculosis* by PCR and Inciting Curve Analysis

*Mycobacterium tuberculosis* was detected by PCR and melting curve analysis using Qprobe having substitution of a guanine base present within 1 to 7 bases from the cytosine base conjugated with a fluorescent dye with a hypoxanthine base. Specifically, PCR was performed using purified genomic DNA from *Mycobacterium tuberculosis* strain R37Rv having the nucleotide sequence set forth in SEQ ID NO: 26 (hereinafter, referred to as "TB genome") as a target nucleic acid and using QProbe (hereinafter, referred to as "TB-IQP1" and "TB-IQP2", respectively) having substitution of the guanine bases 1 or 2 bases apart from the cytosine base conjugated with a fluorescent dye with hypoxanthine bases to amplify TB genome, which was detected by the melting curve analysis. In addition, TB genome was detected using QProbe with no substitution (hereinafter, referred to as "TB-QP") as Comparative Example.

(Materials)

Target nucleic acid: purified genomic DNA from *Mycobacterium tuberculosis* strain 1-137Rv having the nucleotide sequence set forth in SEQ ID NO: 26 (TB genome).

PCR primer: primers having the nucleotide sequences set forth in SEQ ID NO: 27 to 28 (TB-dnaJ1-PCR26 and TB-dnaJ1-PCR11), 10 µM.

10×PCR buffer
dNTPs 2 mM
MgSO₄ 25 mM
KOD plus DNA polymerase 1 U
QProbe: probes comprising oligonucleotides having SEQ ID NOs: 27 to 29 and BODIPY (R)-FL conjugated with a terminal cytosine base in the oligonucleotide (TB-QP, TB-IQP1, and TB-1QP2), 2 µM.

Details of TB-dnaJ1-PCR26 and TB-dnaJ1-PCR11 and TB-QP, TB-IQp1, and TB-IQP2 are set forth in Table 6 below.

TABLE 6

| Name | | SEQ ID NO: | Buse sequence (5'-3') of primers and probes |
|---|---|---|---|
| Target nucleic acid | TB genome | 26 | — |
| PCR | TB-dnaJ1-PCR26 | 27 | CCAAGCGCAAGGAGTACGACGAA |

TABLE 6-continued

| Name | | SEQ ID NO: | Buse sequence (5'-3') of primers and probes |
|---|---|---|---|
| primers | TB-dnaJ1-PCR11 | 28 | GAACAAGCCACCGAACAAGTCACCGAT |
| QProbe | TB-QP | 29 | CGGTGGAGACGGCGC |
|  | TB-IQP1 | 30 | GTCGGTGGAGACGGC<u>I</u>C |
|  | TB-IQP2 | 31 | GGTCGGTGGAGACG<u>I</u>C<u>I</u>C |

(Method)

The PCR reaction solution containing the following reagents was prepared.

[PCR Reaction Solution (10.00 µL)]
Distilled water 2.20 µL
TB-dnaJ1-PCR26V2 0.250 µM 0.25 µL
TB-dnaJ1-PCR11 1.500 µM 1.50 µL
QProbe (TB-QP, TB-IQP1, or TB-IQP2) 0.250 µM 1.25 µL
Buffer solution 1×1.00 µL
dNTPs 0.2 mM 1.00 µL
MgSO₄ 4.0 mM 1.60 µL
KOD plus DNA polymerase 0.2 U 0.20 µL
TB genome 20.0 ng 1.00 µL PCR reactions and melting curve analysis were performed under the following conditions. In the melting curve analysis (item 6) below), fluorescence intensity was measured while increasing the temperature of reaction solution from 40° C. to 75° C. The temperature was increased at 0.5° C./s and the measurement was performed five times for every degree Celsius. Based on the measured fluorescence intensity, the change of the fluorescence intensity (–(d/dt) fluorescence intensity) was determined. In the measurement, fluorescence intensity at 510 nm was measured at an excitation wavelength of 465 nm using LightCycler (R) 480 Instrument II (F. Hoffmann-La Roche Ltd). The same measurement was performed twice. [Conditions for PCR reaction and melting curve analysis]

1) 94° C. 2 minutes
2) 98° C. 1 second
3) 65° C. 5 seconds
4) 94° C. 1 minute
5) 40° C. 1 minute
6) 40° C. to 75° C.

In the PCR reaction, the steps 2)-4) were repeated 50 cycles.

(Result)

Figure 7:
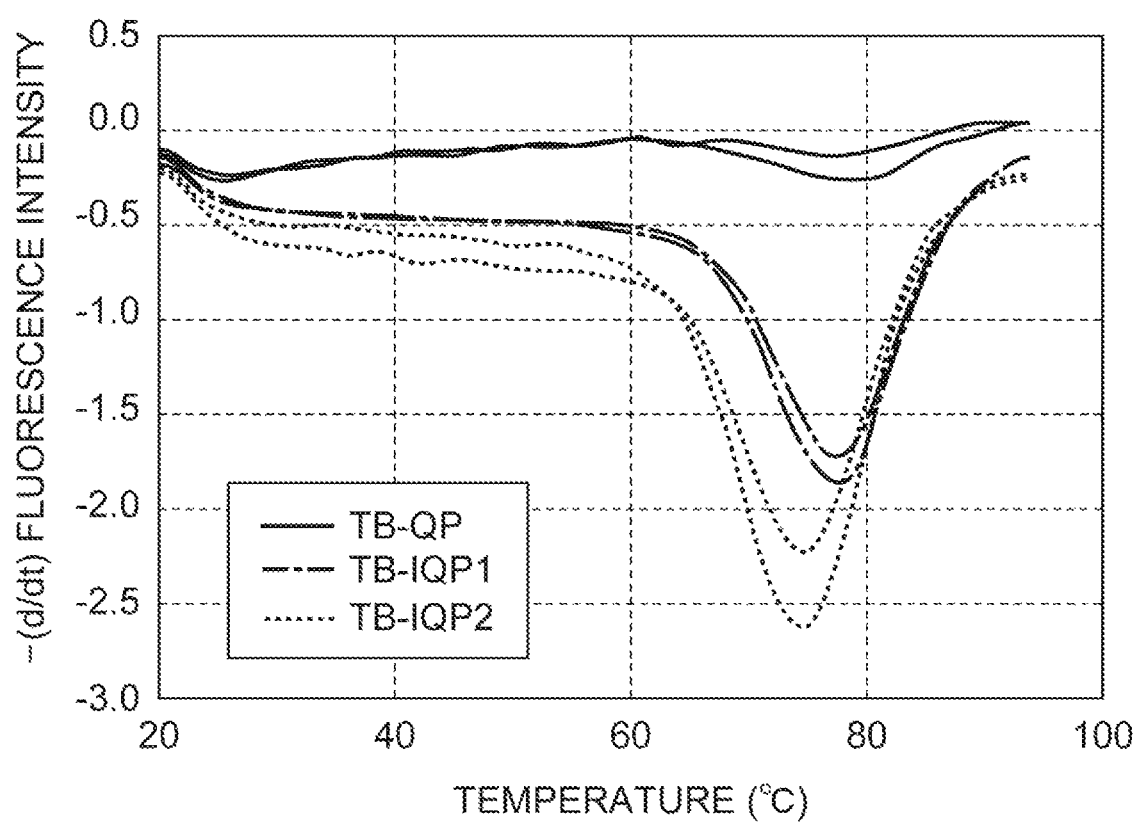
FIG. 7 illustrates a result of detection of *Mycobacterium tuberculosis* by PCR and the melting curve analysis.

When using a probe having substitution of a guanine base present within 1 to 7 bases from a cytosine base conjugated with a fluorescent dye with a hypoxanthine base (TB-IQP1 or TB-IQP2), the change in fluorescence intensity was increased in comparison with that when using a probe having no substitution of a guanine base present within 1 to 7 bases from the cytosine base conjugated with a fluorescent dye with a hypoxanthine base (TB-QP) (FIG. 7). In other words, when using TB-IQP1 or TB-IQP2, the change in fluorescence intensity by hybridization with a target nucleic acid is greater than when using TB-QP. Moreover, when using a probe having substitution of a plurality of guanine bases present within 1 to 7 bases from the cytosine base conjugated with a fluorescent dye with hypoxanthine bases (TB-IQP2), the change in fluorescence intensity was increased in comparison with that when using a probe having substitution of a guanine base present within 1 to 7 bases from the cytosine base conjugated with a fluorescent dye with a hypoxanthine base (TB-1QP1) (FIG. 7). In other words, when using TB-IQP2, the change in fluorescence intensity by hybridization with a target nucleic acid was even greater relative to that when using TB-IQP1.

The result of Example 6 indicated that the sensitivity of detection of Mycobacterium tuberculosis by PCR reactions and melting curve analysis can be increased by substituting a guanine base present within 1 to 7 bases from, the cytosine base conjugated with a fluorescent dye with a hypoxanthine base. Moreover, it was found that the sensitivity of detection can be increased by substituting a plurality of guanine bases present within 1 to 7 bases from the cytosine base conjugated with a fluorescent dye with hypoxanthine bases.

[Example 7] Detection of SNP

A target nucleic acid having SNP was detected by melting curve analysis using (Probe having substitution of a base in the oligonucleotide facing "single nucleotide polymorphism" locating 1 base apart from the cytosine base conjugated with a fluorescent dye with a base selected from hypoxanthine, thymine, cytosine, and adenine.

(Materials) Target nucleic acid: synthetic DNAs having the nucleotide sequences set forth in SEQ ID NOs: 32 to 35 (hereinafter, also referred to as "Model A", "Model G", "Model T", and "Model C", respectively).

QProbe: Probes comprising oligonucleotides having SEQ ID NOs: 36 to 40 and conjugated with TAMRA at a terminal cytosine base in the oligonucleotides (hereinafter, also referred to as "SNP-GQP", "SNP-IQP", "SNP-AQP", "SNP-TQP", and "ANP-CQP", respectively), 2 μM.

Hybridization buffer: a buffer containing KCl, Tris-HCl (pH 8.0), and TWEEN-20™ (polyoxyethylene (20) sorbitan monostearate).

The target nucleic acid and QProbes were synthesized by Japan Bio Services Co., LTD by request.

Details of the target nucleic acid and QProbe are set forth in Table 7.

TABLE 7

| | Name | SEQ ID NO: | Base sequence (5'-3') |
|---|---|---|---|
| Target nucleic acid | Model A | 32 | GATTTTTTTTTTTTTTTTTC |
| | Model G | 33 | GGTTTTTTTTTTTTTTTTTC |
| | Model T | 34 | GTTTTTTTTTTTTTTTTTTC |
| | Model C | 35 | GCTTTTTTTTTTTTTTTTTC |
| QProbe | SNP-GQP | 36 | GAAAAAAAAAAAAAAAAAGC |
| | SNP-IQP | 37 | GAAAAAAAAAAAAAAAAAIC |
| | SNP-AQP | 38 | GAAAAAAAAAAAAAAAAAAC |
| | SNP-TQP | 39 | GAAAAAAAAAAAAAAAAATC |
| | SNP-CQP | 40 | GAAAAAAAAAAAAAAAAACC |

3.2 μL of a target nucleic acid (Model A, Model G, Model T, or Model C), 0.5 μL of SNP-GQP, and 21.3 μL of the hybridization buffer were mixed to prepare a mixture containing 1.28 μM target nucleic acid (model A, model G, model T or model C), 0.04 μM SNP-GQP, 50 mM KCl, 10 mM Tris-HCl (pH 8.0), and 0.1% Tween 20 TWEEN-20™ (polyoxyethylene (20) sorbitan monostearate) at final concentrations. The melting curve analysis was performed by measuring fluorescence intensity while lowering the temperature of the mixture from 95° C. to 20° C. The temperature was decreased at −0.06° C./s and the measurement was performed five times for every degree Celsius. Based on the measured fluorescence intensity, the change in fluorescence intensity (-(d/dt) fluorescence intensity) was determined. In the measurement, fluorescence intensity at 580 nm was measured at an excitation wavelength of 533 nm using LightCycler (R) 480 Instrument II (F. Hoffmann-La Roche Ltd). The same measurement was performed twice. The melting curve analysis was performed in the same manner as that with SNAP-GQP except that SNP-IQP, SNP-AQP, SNP-TQP, and SNP-CQP were used instead of SNP-GQP.

(Result)

When using a probe (SNP-IQP) having substitution of a base in the oligonucleotide facing "single nucleotide polymorphism" present within 1 to 7 bases from the cytosine base conjugated with a fluorescent dye with a hypoxanthine base, the quenching initiation temperature was lower in the order of Model C, Model A, Model U, and Model T (FIG. 8 (a)). Thus, it was found that SNP can be detected for every kind of the mutated base by using SNP-IQP since the quenching initiation temperatures for Model C, Model A, Model G, and Model T are each different. It was found that even when using a probe (SNP-IQP) having substitution of a base in the oligonucleotide facing "single nucleotide polymorphism" present within 1 to 7 bases from the cytosine base conjugated with a fluorescent dye with a thymine base, SNP can be detected for every kind of the mutated base by using SNP-TQP since the quenching initiation temperatures for Model C, Model A, Model and Model T are each different (FIG. 8 (b)).

[Example 8] Detection of Target Nucleic Acids Having Stepwisely Varying Positions of SNP The target nucleic acids having stepwisely varying positions of SNP was detected by melting curve analysis using Qprobe having substitution of a base in the oligonucleoticle facing "single nucleotide polymorphism" present within 1 to 7 bases from the cytosine base conjugated with a fluorescent dye with a hypoxanthine base.

(Materials) Target nucleic acid: synthetic DNAs having the nucleotide sequences set forth in SEQ ID NOs: 32 to 35, 41 to 44, and 46 to 49 (Synthetic DNAs having the nucleotide sequences 41 to 44 and 46 to 49 are also referred to as "Model A3", "Model G5", "Model T3", and "Model C5" and "Model A5", "Model G5", "Model T5", and "Model C5", respectively). QProbe: probes comprising oligonucleotides having SEQ NOs: 37, 45, and 50 and conjugated with TAMRA at a terminal cytosine base in the oligonucleotide (probes comprising oligonucleotides having SEQ 11) NOs: 45 and 50 and conjugated with TAMRA at a terminal cytosine base in the oligonucleotide are also referred to as "SNP-IQP3" and "SNP-IQP5", respectively), 2 μM.

Hybridization buffer: a buffer containing KCl, Tris-HCl (pH 8.0), and TWEEN-20™ (polyoxyethylene (20) sorbitan monostearate).

The target nucleic acid and QProbes were synthesized by Japan Bio Services Co., LTD by request.

Details of the target nucleic acids and QProbes are set forth in Table 8.

TABLE 8

| | Name | SEQ ID NO: | Base sequence (5'-3') | Position of SNP (distance (bases) from terminal guanine base to SNP in target nucleic acid) |
|---|---|---|---|---|
| Target nucleic acid | Model A | 32 | GATTTTTTTTTTTTTTTTTC | 1 |
| | Model G | 33 | GGTTTTTTTTTTTTTTTTTC | 1 |
| | Model T | 34 | GTTTTTTTTTTTTTTTTTTC | 1 |
| | Model C | 35 | GCTTTTTTTTTTTTTTTTTC | 1 |
| QProbe | SNP-IQP | 37 | GAAAAAAAAAAAAAAAAAIC | — |
| Target nucleic acid | Model A3 | 41 | GTTATTTTTTTTTTTTTTTC | 3 |
| | Model G3 | 42 | GTTGTTTTTTTTTTTTTTTC | 3 |
| | Model T3 | 43 | GTTTTTTTTTTTTTTTTTTC | 3 |
| | Model C3 | 44 | GTTCTTTTTTTTTTTTTTTC | 3 |
| QProbe | SNP-IQP3 | 45 | GAAAAAAAAAAAAAAAIAAC | — |
| Target nucleic acid | Model A5 | 46 | GTTTTATTTTTTTTTTTTTC | 5 |
| | Model G5 | 47 | GTTTTGTTTTTTTTTTTTTC | 5 |
| | Model T5 | 48 | GTTTTTTTTTTTTTTTTTTC | 5 |
| | Model C5 | 49 | GTTTTCTTTTTTTTTTTTTC | 5 |
| QProb | SNP-IQP5 | 50 | GAAAAAAAAAAAAAIAAAAC | — |

(Method)

Melting curve analysis was performed using Model A, Model Model T, and Model C as target nucleic acids in the same manner as that with SNP-IQP in Example 7. Moreover, melting curve analysis was performed in the same manner as Example 7 except that Model A3, Model G3, Model T3, and Model C3 were used as target nucleic acids instead of Model A, Model Model T, and Model C and SNP-IQP3 was used instead of SNP-GQP, SNP-IQP, SNP-AQP, SNP-TQP, and ANP-CQP as Qprobe. Moreover, melting curve analysis was performed in the same manner as Example 7 except that Model A5, Model G5, Model T5, and Model C5 were used as target nucleic acids instead of Model A, Model Model T, and Model C and SNP-IQP5 was used as Qprobe instead of SNP-GQP, SNP-IQP, SNP-AQP, SNP-TQP, and ANP-CQP.

(Result)

Figure 9A:
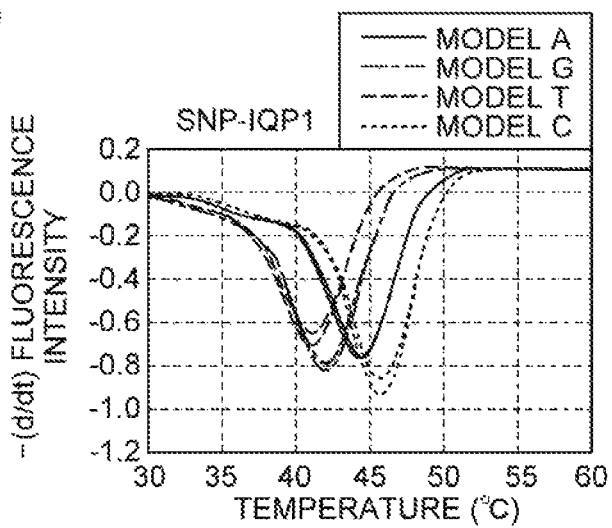
FIGS. 9(a) to 9(c) illustrate results of detection of target nucleic acids having stepwisely varying positions of SNP.
Figure 9B:
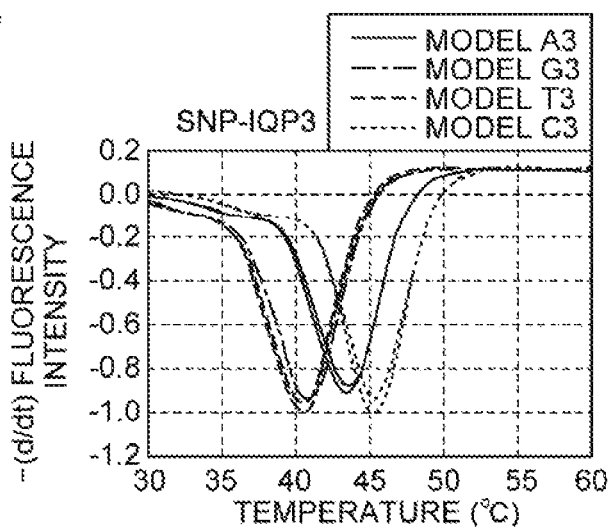
Figure 9C:
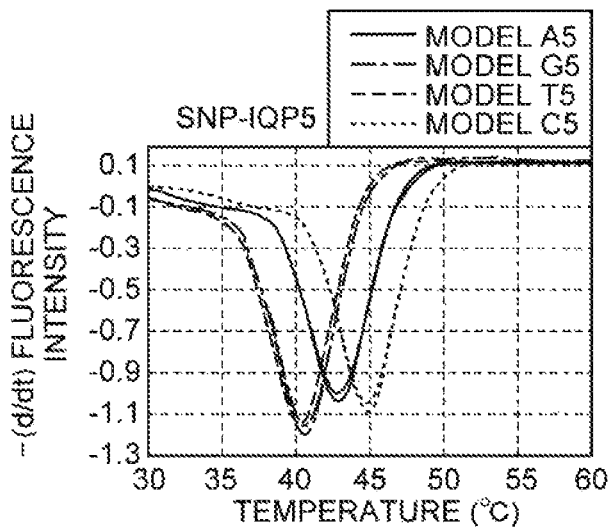

It was found that the kind (A, C, and T (or G)) of the mutated base can be determined when the target nucleic acids having stepwisely varying positions of SNP were detected with SNP-IQP3 since the quenching initiation temperatures for Model A3, Model C3, and Model T3 (or Model G3) are each different (FIG. 9 (b)). Specifically, when Model A3, Model G3, Model T3, and Model C3 were detected with SNP-IQP3, the quenching initiation temperatures were lower in the order of Model C3, Model A3, and Model T3 (or Model G3) (FIG. 9 (b)). Moreover, it was found that the kind (A, C, and T (or G)) of the mutated base can be detected when Model A5, Model G5, Model T5, and Model C5 were detected with SNP-IQP5 since the quenching initiation temperatures for Model A5, Model C5, and Model T5 (or Model G5) are each different FIG. 9 (c)). Specifically, the quenching initiation temperatures were lower in the order of Model C5, Model A5, and Model G5 (or Model T5) (FIG. 9 (c)).

The result of Example $ indicated that SNP in target nucleic acids having stepwisely varying positions of SNP can be detected by using a probe having substitution of a base in the oligonucleotide facing "single nucleotide polymorphism" present within 1 to 7 bases from the cytosine base conjugated with a fluorescent dye with a hypoxanthine base.

---

The invention claimed is:

1. A first nucleic acid probe for detecting a target nucleic acid amplified by a nucleic acid amplification, wherein
the target nucleic acid comprises a probe-binding region with which the first nucleic acid probe hybridizes;
at least one terminal of the probe-binding region is a guanine base, and one or more cytosine bases are present within 1 to 7 bases from the guanine base in the probe-binding region;
the first nucleic acid probe comprises an oligonucleotide having a cytosine base facing the guanine base on a terminal and a fluorescent dye conjugated to the cytosine base;
the fluorescent dye is a fluorescent dye that is quenched by the interaction with a guanine base; and
the oligonucleotide is complementary to the nucleic acid in the probe-binding region except the cytosine base present within 1 to 7 bases from the terminal guanine base, and one or more bases in the oligonucleotide facing the one or more cytosine bases are a guanine base or a base having no fluorescence-quenching effect, provided that the base in the oligonucleotide facing the cytosine base closest to the terminal guanine base among the one or more cytosine bases is a base having no fluorescence-quenching effect, and
wherein the base having no fluorescence-quenching effect is a hypoxanthine base.

2. A second nucleic acid probe for detecting a target nucleic acid amplified by a nucleic acid amplification,
wherein the target nucleic acid comprises a probe-binding region with which the second nucleic acid probe hybridizes;
at least one terminal of the probe-binding region is a guanine base, and one or more single nucleotide polymorphisms are present within 1 to 7 bases from the guanine base in the probe-binding region;
the second nucleic acid probe comprises an oligonucleotide having a cytosine base facing the guanine base on a terminal and a fluorescent dye conjugated to the cytosine base;
the fluorescent dye is a fluorescent dye that is quenched by the interaction with a guanine base;
the oligonucleotide is complementary to the nucleic acid in the probe-binding region except the one or more single nucleotide polymorphisms within 1 to 7 bases from the terminal guanine base; one or more bases in the oligonucleotide facing the one or more single nucleotide polymorphisms are a guanine base or a base having no fluorescence-quenching effect; provided that the base in the oligonucleotide facing the single nucleotide polymorphism closest to the terminal guanine base among the one or more single nucleotide polymorphisms is a base having no fluorescence-quenching effect, and wherein the base having no fluorescence-quenching effect is a hypoxanthine base.

3. A method for detecting a target nucleic acid, comprising the steps of:
mixing the first nucleic acid probe for detecting a target nucleic acid and a sample to prepare a mixture;
measuring fluorescence intensity from the mixture; and
detecting the target nucleic acid based on the fluorescence intensity,
wherein the target nucleic acid comprises a probe-binding region with which the first nucleic acid probe hybridizes;
at least one terminal of the probe-binding region is a guanine base, and one or more cytosine bases are present within 1 to 7 bases from the guanine base in the probe-binding region;
the first nucleic acid probe comprises an oligonucleotide having a cytosine base facing the guanine base on a terminal and a fluorescent dye conjugated to the cytosine base;

the fluorescent dye is a fluorescent dye that is quenched by the interaction with a guanine base; and the oligonucleotide is complementary to the nucleic acid in the probe-binding region except the cytosine base present within 1 to 7 bases from the terminal guanine base, and one or more bases in the oligonucleotide facing the one or more cytosine bases are a guanine base or a base having no fluorescence-quenching effect, provided that the base in the oligonucleotide facing the cytosine base closest to the terminal guanine base among the one or more cytosine bases is a base having no fluorescence-quenching effect, wherein the base having no fluorescence-quenching effect is a hypoxanthine base, and the sample comprises an amplified product obtained by a nucleic acid amplification reaction using a test nucleic acid as a template.

4. The method according to claim 3, wherein the detection is conducted by melting curve analysis.

5. The method
according to claim 3
wherein the amplification reaction is a polymerase chain reaction comprising repeated cycles of a denaturation stage, an annealing stage, and an extension stage and
comprising, in the annealing stage, measuring fluorescence intensity from the mixture.

6. A method for detecting a target nucleic acid, comprising the steps of:

mixing the second nucleic acid probe for detecting a target nucleic acid and a sample to prepare a mixture;

measuring fluorescence intensity from the mixture; and detecting the target nucleic acid based on the fluorescence intensity, wherein the target nucleic acid comprises a probe-binding region with which the second nucleic acid probe hybridizes;

at least one terminal of the probe-binding region is a guanine base, and one or more single nucleotide polymorphisms are present within 1 to 7 bases from the guanine base in the probe-binding region;

the second nucleic acid probe comprises an oligonucleotide having a cytosine base facing the guanine base on a terminal and a fluorescent dye conjugated to the cytosine base;

the fluorescent dye is a fluorescent dye that is quenched by the interaction with a guanine base;

the oligonucleotide is complementary to the nucleic acid in the probe-binding region except the one or more single nucleotide polymorphisms within 1 to 7 bases from the terminal guanine base; one or more bases in the oligonucleotide facing the one or more single nucleotide polymorphisms are a guanine base or a base having no fluorescence-quenching effect; provided that the base in the oligonucleotide facing the single nucleotide polymorphism closest to the terminal guanine base among the one or more single nucleotide polymorphisms is a base having no fluorescence-quenching effect, and wherein the base having no fluorescence-quenching effect is a hypoxanthine base, and the sample comprises an amplified product obtained by a nucleic acid amplification reaction using a test nucleic acid as a template.

7. The method according to claim 6, wherein the detection is carried out by melting curve analysis.

8. The method according to claim 7, wherein the single nucleotide polymorphism is detected by melting curve analysis.

* * * * *